(12) United States Patent
Tsunoda et al.

(10) Patent No.: US 7,550,562 B2
(45) Date of Patent: Jun. 23, 2009

(54) PEMPHIGUS MONOCLONAL ANTIBODY

(75) Inventors: Kazuyuki Tsunoda, Tokyo (JP); Masayuki Amagai, Tokyo (JP); Takeji Nishikawa, Tokyo (JP); Shigeo Koyasu, Tokyo (JP)

(73) Assignee: Keio University, Tokyo (JP)

( * ) Notice: Subject to any disclaimer, the term of this patent is extended or adjusted under 35 U.S.C. 154(b) by 417 days.

(21) Appl. No.: 10/488,673

(22) PCT Filed: Sep. 4, 2002

(86) PCT No.: PCT/JP02/08987

§ 371 (c)(1), (2), (4) Date: Aug. 12, 2004

(87) PCT Pub. No.: WO03/020769

PCT Pub. Date: Mar. 13, 2003

(65) Prior Publication Data

US 2005/0025760 A1 Feb. 3, 2005

(30) Foreign Application Priority Data

Sep. 4, 2001 (JP) ............................. 2001-267653

(51) Int. Cl.
*C07K 14/00* (2006.01)
*C07K 17/00* (2006.01)

(52) U.S. Cl. ..................................... 530/350

(58) Field of Classification Search ................ None
See application file for complete search history.

(56) References Cited

FOREIGN PATENT DOCUMENTS

JP 08-188540 7/1996

OTHER PUBLICATIONS

Proby et al., 2000, British J. of Dermatology, vol. 142: 321-330.*
Ishikawa et al., 1994, Mammalian Genome, vol. 5: 803-804.*
Amagai et al., 1992, J. Clin. Invest. vol. 90: 919-926.*
Tchernev et al., 2006, Tissue Antigens, vol. 68: 280-286.*
Sekiguchi et al.,2000, J Derm. Sci. vol. 23: 197.*

K. Tsunoda et al., "Development of anti-desmoglein 2(Dsg3) pathogenic monoclonal antibody using active disease mouse model for pemphigus vulgaris (PV)," *J. Invest. Dermatol.*, vol. 117, No. 2, pp. 349, 028, Aug. 2001.
K. Tsunoda et al., "Production of anti-desmoglein 3 mouse monoclonal antibodies using active disease mouse model for pemphigus," *J. Invest. Dermatol*, vol. 114, No. 4, pp. 846, 579, 2000.
M. Amagi et al., "Use of autoantigen-knockout mice in developing an active autoimmune disease model for pemphigus," *J. Clin. Invest.* vol. 105, No. 5, p. 625-31, 2000.
M. Amagi et al, "Antibodies against desmoglein 3 (pemphigus vulgaris antigen) are present in sera from patients with paraneoplastic pemphigus and cause acantholysis in vivo in neonatal mice," *J. Clin. Invest.*, vol. 102, No. 4, p. 775-82, 1998.
M. Amagi et al., "Autoantibodies against a novel epithelial cadherin in pemphigus vulgaris, a disease of cell adhesion," *Cell*, vol. 67, No. 5, p. 869-77, 1991.
K. Tsunoda et al., "A pathogenic antidesmoglein 3 monoclonal antibody recognizes the N-terminal adhesive region of desmoglein 3," *J. Invest. Dermatol.*, vol. 119, No. 1, pp. 228, 125, Jul. 2002.
M. Ohyama et al., "Immunologic and histopathologic characterization of active disease model mouse for pemphigus vulgaris," *J. Invest. Dermatol.*, vol. 117, No. 2, pp. 459, 416, Aug. 2001.
H. Ishikawa et al., "Molecular cloning of the mouse desmoglein 3 gene (Dsg3): genomic structure and homology with the human gene," *J. Invest. Dermatol.*, vol. 106, No. 4, pp. 848, 258, 1996.
Y. Futei et al., "Use of domain-swapped molecules for conformational epitope mapping of desmoglein 3 in pemphigus vulgaris," *J. Invest. Dermatol.*, vol. 115, No. 5, pp. 829-834, 2000.

* cited by examiner

*Primary Examiner*—G. R Ewoldt
*Assistant Examiner*—Amy E Juedes
(74) *Attorney, Agent, or Firm*—Locke Lord Bissell & Liddell, LLP

(57) ABSTRACT

The present invention provides a monoclonal antibody having a pathogenic activity that can induce pemphigus lesion, a peptide specifically recognized by the monoclonal antibody and useful as a therapeutic drug for pemphigus autoimmune disease, etc. As anti-mouse Dsg3 antibody-producing cells are present in the splenocytes of pemphigus vulgaris mouse model constructed by using autoantigen knockout mouse, cell fusion was conducted with the splenocytes of said mouse model and mouse myeloma cells using polyethyleneglycol, hybridomas were constructed, and monoclonal antibodies against Dsg3 were constructed. Among them, a monoclonal antibody having a pathological activity that can induce pemphigus lesions was screened, the base sequence and amino acid sequence in its variable region (heavy chain, light chain) was determined, and the specific epitope part was identified.

1 Claim, 7 Drawing Sheets

FIG 8 heavy chain (SEQ ID NO: 4)

```
  1 CAGGTCCAACTGCAGCAGTCTGGGACTGAACTGGTGAAGCCTGGGGCTTCAGTGAAGCTG   60
  1  Q  V  Q  L  Q  Q  S  G  T  E  L  V  K  P  G  A  S  V  K  L   20
 61 TCCTGCAAGTCTTCTGGCTACACCTTCACCAGCTACTGGATAAACTGGGTGAAGCAGAGG  120
 21  S  C  K  S  S  G  Y  T  F  T  S  Y  W  I  N  W  V  K  Q  R   40
121 CCTGGACAGGGCCTTGAGTGGATTGGAAATATTAATCCTAGCAATGGTGGTATTAACTAT  180
 41  P  G  Q  G  L  E  W  I  G  N  I  N  P  S  N  G  G  I  N  Y   60
181 AATGAGAAGTTCAAGAGTAAGGCCACACTGACTGTAGACAAATCCTCCAGCACAGCCTAC  240
 61  N  E  K  F  K  S  K  A  T  L  T  V  D  K  S  S  S  T  A  Y   80
241 ATGCAACTCAAGAGCCTGACATCTGAGGACTCTGCGGTCTATTATTGTGCAAGGGGGGGC  300
 81  M  Q  L  K  S  L  T  S  E  D  S  A  V  Y  Y  C  A  R  G  G  100
301 TATGATGGTTACCCCTGGGGCCAAGGCACCACGGTCACCGTTTCCTC               347
101  Y  D  G  Y  P  W  G  Q  G  T  T  V  T  V  S                 116
``` light chain (SEQ ID NO: 6)

```
  1 GACATTCAGATGACACAGTCTCCCAAATTCCTGCTTGTATCAGCAGGAGACAGGGTTACC   60
  1  D  I  Q  M  T  Q  S  P  K  F  L  L  V  S  A  G  D  R  V  T   20
 61 ATAACCTGCAAGGCCAGTCAGAGTGTGAGTTATGATGTAGCTTGGTATCAACAGAAGCCA  120
 21  I  T  C  K  A  S  Q  S  V  S  Y  D  V  A  W  Y  Q  Q  K  P   40
121 GGGCAGTCTCCGAAATTGCTGATATCCTATGCATCCAATCGCTACACTGGAGTCCCTGAT  180
 41  G  Q  S  P  K  L  L  I  S  Y  A  S  N  R  Y  T  G  V  P  D   60
181 CGCTTCACTGGCAGTGGATATGGGTCGGATTTCACTTTCACCATCAGCACTGTGCAGACT  240
 61  R  F  T  G  S  G  Y  G  S  D  F  T  F  T  I  S  T  V  Q  T   80
241 GAAGACCTGGCAGTTTATTTCTGTCAGCAGGATTATAGCTCTCCGTGGACGTTCGGTGGA  300
 81  E  D  L  A  V  Y  F  C  Q  Q  D  Y  S  S  P  W  T  F  G  G  100
301 GGCACCAAGCTGGAGCTGAAACGT                                      324
101  G  T  K  L  E  L  K  R                                      108
```

PEMPHIGUS MONOCLONAL ANTIBODY

TECHNICAL FIELD

The present invention relates to a pemphigus monoclonal antibody having a pathological activity that can induce pemphigus lesions, a peptide specifically recognized by the pemphigus monoclonal antibody that is useful as a therapeutic drug for pemphigus autoimmune disease, etc.

BACKGROUND ART

Pemphigus vulgaris (PV) is an autoimmune blistering disease of the skin and mucous membranes, which is histologically characterized by intraepidermal blister formation and immunopathologically characterized by the IgG autoantibody against the keratinocyte cell surface (Stanley, J. R. Pemphigus. In Dermatology in General Medicine. I. M. Freedberg, A. Z. Eisen, K. Wolff, K. F. Austen, L. A. Goldesmith, S. I. Katz, and T. B. Fitzpatrick, eds. McGraw-Hill, New York, 654-666 (1998)). Clinically, patients with pemphigus vulgaris exhibit extensive flaccid blister and erosion. These can occur in every stratified squamous epithelium. Pemphigus vulgaris can be lethal, since failing to conduct an appropriate therapy results in the induction of the leakage of body fluid or secondary bacterial infection caused by the focus developed at a wide range in the skin. The prognosis of pemphigus is being improved by systemic administration of corticosteroid and immunosuppression therapy, however, its mortality rate remains very high because of the death due to the complication of therapy.

The target antigen of pemphigus vulgaris was first identified by immunoprecipitation of keratinocyte extracts as a 130 kD glycoprotein (J. Clin. Invest. 70, 281-288, 1982; J. Clin. Invest. 74, 313-320, 1984). Then, cDNA of pemphigus vulgaris antigen was isolated by immunoscreening human keratinocyte expression libraries, with the use of an affinity-purified autoantibody specific to the pemphigus vulgaris antigen (Cell, 67, 869-877, 1991). Base sequence analysis showed that pemphigus vulgaris antigen belongs to the cadherin supergene family of cell-cell adhesion molecules. Pemphigus vulgaris antigen is a desmosomal transmembrane protein (J. Cell Biol. 122, 409-415, 1993) and was named desmoglein3 (Dsg3) (Adv. Dermatol. 11, 319-352, 1996).

There exist many evidences indicating that the IgG autoantibody against Dsg3 proteins have an aetiologic role for pemphigus vulgaris. Firstly, it is reported by indirect immunofluorescence (Br. J. Dermatol. 84, 7-13, 1971) or ELISA (J. Immunol. 159, 2010-2017, 1997; Br. J. Dermatol. 140, 351-357, 1999), that the chronological disease activity correlates with blood antibody titer. Secondly, the neonates of mothers with pemphigus vulgaris have transient disease due to maternal IgG that crosses through the placenta (Pediatrics 78, 1102-1105, 1986). As the maternal IgG is catabolized, the symptoms are relieved. Thirdly, the IgG derived from patients with pemphigus vulgaris, without complement or inflammatory cells, can induce blister formation in tissue-cultured skin (J. Invest. Dermatol. 67, 254-260, 1976; J. Exp. Med. 157, 259-272, 1983). Fourthly, passive transfer of IgG derived from patient sera to neonatal mice results in an intraepidermal blister formation with typical histological findings (N. Engl. J. Med. 306, 1189-1196, 1982). Fifthly, when the patient sera is removed by immunoabsorption with recombinant Dsg3 protein (rDsg3) which comprises an extracellular domain, the pathogenicity of the sera is removed, thereby inhibiting the blister formation in neonatal mice (J. Clin. Invest. 94, 59-67, 1994). Lastly, the antibody affinity-purified by rDsg3 has antigenicity, and forms a blister with histological findings of pemphigus vulgaris in neonatal mice (J. Clin. Invest. 90, 919-926, 1992; J. Clin. Invest. 102, 775-782, 1998). As can be seen from these studies, pemphigus vulgaris is one of the autoimmune diseases wherein its characteristic is most determined especially in the process after the production of autoantibody. Therefore, at present, pemphigus vulgaris is said to be an excellent disease model for organ-specific autoimmune disease, in order to study the cell mechanism of autoantibody production or breakdown of self-tolerance, and also to develop a disease-specific therapeutic method.

Based on the hypothesis that pathogenic antibodies are not produced in the body of mice due to the self-tolerance against Dsg3 proteins, the present inventors developed a method for generating mice that show phenotype of pemphigus vulgaris (PV mouse model), based on the finding that the immune system of Dsg3-deficient mice generated by gene targeting techniques is not exposed to Dsg3 proteins at the developmental stage, and therefore, self-tolerance against Dsg3 is not acquired (Japanese Patent Application Nos. H11-91408 and 2001-156126). That is, a method for generating mice that show phenotype of pemphigus vulgaris, comprised of the following steps: mice deficient in Dsg3 gene are immunized with recombinant Dsg3 protein (rDsg3 protein), splenocytes are prepared from the immunized mice, the splenocytes prepared are transferred to mice expressing Dsg3 proteins, and an antibody that reacts to Dsg3 proteins is produced or T cells are activated (Japanese Patent Application No. H11-91408), or a method for generating mice that show phenotype of pemphigus vulgaris, comprised of the following steps: splenocytes prepared from mice deficient in naive Dsg3 gene are prepared to $5 \times 10^7$ cells/mouse, the cells are transferred to the mice expressing Dsg3 proteins, and an antibody that reacts to Dsg3 proteins is produced or T cells are activated (Japanese Patent Application No. 2001-156126).

As mentioned above, pemphigus vulgaris is an autoimmune blistering disease against Dsg3, a cell-cell adhesion molecule, wherein the autoantibody having a pathogenicity involved in its onset is polyclonal, and the pathogenicity of their individual autoantibody is unknown. The PV model mice developed by the present inventors mentioned above are induced with its phenotype by anti-Dsg3 antibody having the pathogenicity. Therefore, it is considered that generating an anti-Dsg3 monoclonal antibody and analyzing the pathogenicity in the individual monoclonal antibodies are useful for the elucidation of the onset mechanism of pemphigus vulgaris at the molecular level, and for the development of antigen-specific antibody elimination therapy. However, to the present, there are no reports of a monoclonal antibody having a pathogenicity that can induce pemphigus vulgaris lesion. The object of the present invention is to provide a monoclonal antibody having a pathogenic activity that can induce pemphigus vulgaris lesion that is thought to be useful for the elucidation of the onset mechanism of pemphigus vulgaris at the molecular level, and for the development of antigen-specific antibody elimination therapy, a peptide specifically recognized by the monoclonal antibody thought to be useful as a therapeutic drug for pemphigus autoimmune disease that, etc.

DISCLOSURE OF THE INVENTION

The production and induction of an autoantibody having a pathogenicity was difficult due to the presence of immune tolerance against its autoantigen. However, anti-mouse Dsg3 antibody producing cells exist in the splenocytes of PV (pemphigus vulgaris) mouse model generated by using autoantigen knockout mouse. The present inventors conducted cell fusion of the mouse model splenocytes mentioned above and the mouse myeloma cells with polyethyleneglycol (PEG), generated a hybridoma, generated monoclonal antibodies against Dsg3, then, among these monoclonal antibodies generated in large numbers, the monoclonal antibodies having a pathological activity that can induce pemphigus lesion were screened, the base sequence and amino acid sequence in their variable region (heavy chain/light chain) were determined, the specific epitope portion was confirmed, and thus the present invention has completed.

The present invention relates to: a pemphigus monoclonal antibody having a pathogenic activity that can induce pemphigus lesion (1); a pemphigus monoclonal antibody that specifically binds to human and mouse desmoglein (Dsg) 3 and does not show crossreactivity to human and mouse desmoglein (Dsg) 1 (2); the pemphigus monoclonal antibody according to (1) or (2) above that specifically recognizes multiple particular amino acid residues in an amino acid sequence shown by Seq. ID No. 1 or 2 (3); the pemphigus monoclonal antibody according to (3) above, wherein the multiple particular amino acid residues are at least one of the valine residue at position 3, lysine residue at position 7 and proline residue at position 8, and an aspartic acid residue at position 59 of Seq. ID No. 1 or 2 (4); the pemphigus monoclonal antibody according to (1) to (4) above comprising an H chain having an amino acid sequence shown by Seq. ID No. 4 or an amino acid sequence constructed by adding, deleting or substituting one or more amino acid residue in the amino acid sequence shown by Seq. ID No. 4, and functions as an H chain of anti-human Dsg3 monoclonal Fab antibody, and an L chain having an amino acid sequence shown by Seq. ID No. 6 or an amino acid sequence constructed by adding, deleting or substituting one or more amino acid residue in the amino acid sequence shown by Seq. ID No. 6, and functions as an L chain of anti-human Dsg3 monoclonal Fab antibody (5); and an antibody fragment including an antigen binding site comprised of a variable region of the pemphigus monoclonal antibody according to (1) to (5) above (6).

Further, the present invention relates to a pemphigus autoimmune disease animal model wherein pemphigus lesion is induced by administration of a hybridoma that produces the pemphigus monoclonal antibody according to (1) to (5) above (7); a method for screening a therapeutic drug for pemphigus autoimmune disease wherein a test substance is administered to the pemphigus autoimmune disease animal model according to (7) above and the degree of lesion of the pemphigus autoimmune disease in the animal model and/or the antibody titer in the sera is evaluated (8); a method for screening a therapeutic drug for pemphigus autoimmune disease wherein the pemphigus monoclonal antibody according to (1) to (5) above or the antibody fragment according to (6) above is reacted with a test substance, and the antibody titer and/or the degree of the lesion of the pemphigus autoimmune disease is evaluated (9); a peptide containing an epitope specifically recognized by a monoclonal antibody according to any of Seq. ID Nos. 1 to 5 (10); a peptide containing multiple specific amino acid residues in an amino acid sequence shown by Seq. ID No. 1 or 2 and specifically recognized by a pemphigus monoclonal antibody having a pathological activity that can induce pemphigus lesion (11); the peptide according to (11) above, wherein the multiple specific amino acid residues are at least one of the valine residue at position 3, lysine residue at position 7 and proline residue at position 8, and an aspartic acid residue at position 59 of Seq. ID No. 1 or 2 (12); the peptide according to (11) or (12) above, wherein the pemphigus monoclonal antibody specifically binds to human and mouse desmoglein (Dsg) 3 and does not show crossreactivity to human and mouse desmoglein (Dsg) 1 (13); the peptide according to (11) to (13) above, wherein the pemphigus monoclonal antibody comprises an H chain having an amino acid sequence shown by Seq. ID No. 4 or an amino acid sequence constructed by adding, deleting or substituting one or more amino acid residue in the amino acid sequence shown by Seq. ID No. 4, and functions as an H chain of anti-human Dsg3 monoclonal Fab antibody, and an L chain having an amino acid sequence shown by Seq. ID No. 6 or an amino acid sequence constructed by adding, deleting or substituting one or more amino acid residue in the amino acid sequence shown by Seq. ID No. 6, and functions as an L chain of anti-human Dsg3 monoclonal Fab antibody (14); a diagnostic drug for pemphigus autoimmune disease comprising the peptide according to (10) to (14) above as an active ingredient (15); a preventive/therapeutic drug for pemphigus autoimmune disease comprising the peptide according to (10) to (14) above as an active ingredient (16); a preventive/therapeutic drug for pemphigus autoimmune disease wherein the peptide according to (10) to (14) above is used as an active ingredient (17); a hybridoma cell line that produces the pemphigus monoclonal antibody according to (1) to (5) above or a cell line derived from the hybridoma cell line (18).

BRIEF DESCRIPTION OF DRAWINGS

FIG. 8 is a view showing the base sequence and amino acid sequence of the variable region (heavy chain/light chain) of the anti-Dsg3 monoclonal antibody AK23 of the present invention.

BEST MODE OF CARRYING OUT THE INVENTION

Figure 1:
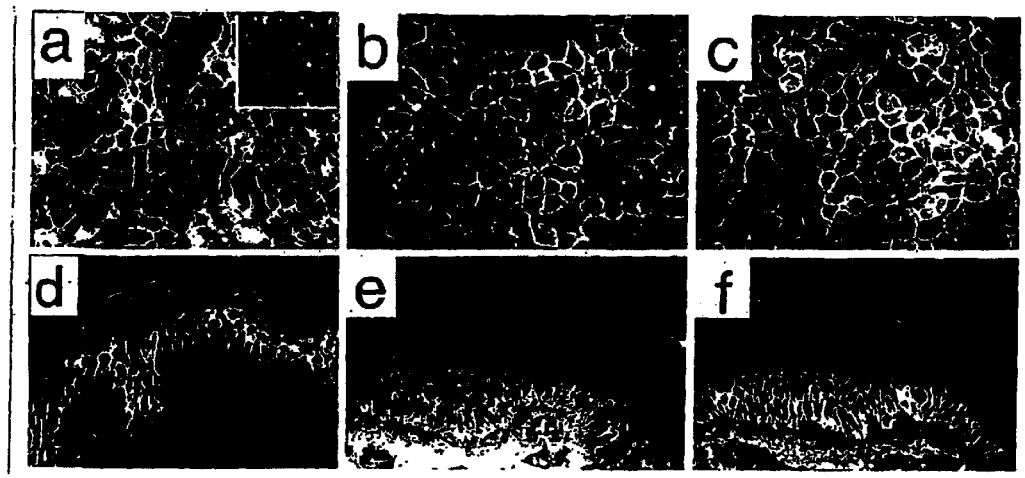
FIG. 1 is a photograph showing the results of indirect immunofluorescence and living cell staining of the anti-Dsg3 monoclonal antibody of the present invention.

As to the pemphigus monoclonal antibody of the present invention, there is no limitation as long as it is a monoclonal antibody having a pathological activity that can induce pemphigus lesion such as pemphigus vulgaris and the like, or a monoclonal antibody that specifically binds to human and mouse Dsg3 and does not show crossreactivity to human and mouse Dsg1. A pathological activity that can induce pemphigus lesions refers to a pathological activity that can induce lesions such as hair loss, weight loss, suprabasilar acantholysis, and the like. As to the pemphigus monoclonal antibody mentioned above, an anti-Dsg3 monoclonal antibody that specifically binds to human and mouse Dsg3 and does not show crossreactivity to human and mouse Dsg1 and has a pathological activity that can induce pemphigus lesions, an anti-Dsg3 monoclonal antibody that specifically binds to mouse Dsg3 and does not show crossreactivity to mouse Dsg1 and has a pathological activity that can induce pemphigus lesions, and an anti-Dsg3 monoclonal antibody that specifically binds to human Dsg3 and does not show crossreactivity to human Dsg1 and has a pathological activity that can induce pemphigus lesions, are preferable. Further, a pemphigus monoclonal antibody that specifically recognizes multiple particular amino acid residues in an amino acid sequence shown by Seq. ID No. 1 or 2, for example, at least one of the valine residue at position 3, lysine residue at position 7 and proline residue at position 8, and an aspartic acid residue at position 59 of Seq. ID No. 1 or 2, and an anti-Dsg3 monoclonal antibody comprising an H chain having an amino acid sequence shown by Seq. ID No. 4 or an amino acid sequence constructed by adding, deleting or substituting one or more amino acid residue in the amino acid sequence shown by Seq. ID No. 4, and functions as an H chain of anti-human Dsg3 monoclonal Fab antibody, and an L chain having an amino acid sequence shown by Seq. ID No. 6 or an amino acid sequence constructed by adding, deleting or substituting one or more amino acid residue in the amino acid sequence shown by Seq. ID No. 6, and functions as an L chain of anti-human Dsg3 monoclonal Fab antibody, can be preferably exemplified. More specifically, the monoclonal antibody of isotype IgG1 κ expressed as AK23 in the example can be given as an example, however, monoclonal antibodies of different isotype or a single chain antibody may also be used.

An example of the method for producing the pemphigus monoclonal antibody of the present invention mentioned above is a method wherein conventional protocols in optional methods such as hybridoma method (Nature 256, 495-497, 1975), trioma method, human B cell hybridoma method (Immunology Today 4, 72, 1983), EBV-hybridoma method (MONOCLONAL ANTIBODIES AND CANCER THERAPY, pp. 77-96, Alan R. Liss, Inc., 1985) and the like are used to make an animal (preferably an animal aside from human) produce antibodies against Dsg3 protein. In this case, it is preferable to use affinity chromatography with a peptide comprising an amino acid sequence shown by Seq. ID No. 2. In addition, based on the base sequence information of a DNA that encodes the H chain variable region shown by Seq. ID No. 3 or a DNA that encodes the L chain variable region shown by Seq. ID No. 5, the pemphigus monoclonal antibody and humanized pemphigus monoclonal antibody of the present invention can be generated, for example, by recombinant DNA techniques according to the known methods for generating humanized antibody (e.g. Nature 322, 323-327, 1988; Science 239, 1534-1536, 1988; Protein Engng. 4, 773-783, 1991; Human Antibodies and Hybridoma 2, 124-134, 1991; Proc. Natl. Acad. Sci. USA 88, 4181-4185, 1991; Proc. Natl. Acad. Sci. USA89, 4285-4289, 1992; J. Immunol. 147, 1149-1154, 1992; Cancer Res. 53, 1-6, 1993).

As to the antibody fragment of the present invention, there is no particular limitation as long as it is an antibody fragment containing an antigen binding site comprised of a variable region of the pemphigus monoclonal antibody of the present invention described above. Examples of the antibody fragment are: $F(ab')_2$ obtained by digesting a monoclonal antibody with pepsin, a Fab' obtained by reducing the $F(ab')_2$, and Fab obtained by digesting a monoclonal antibody with papain. As to the variable region of the pemphigus monoclonal antibody mentioned above, specific examples are an H chain variable region having an amino acid sequence shown by Seq. ID No. 4 or an amino acid sequence constructed by adding, deleting or substituting one or more amino acid residue in the amino acid sequence shown by Seq. ID No. 4, and functions as an H chain of anti-human Dsg3 monoclonal Fab antibody, and an L chain variable region having an amino acid sequence shown by Seq. ID No. 6 or an amino acid sequence constructed by adding, deleting or substituting one or more amino acid residue in the amino acid sequence shown by Seq. ID No. 6, and functions as an L chain of anti-human Dsg3 monoclonal Fab antibody. As described above, the tertiary structure can be predicted by finding out the primary structure including the antigen binding site of the antibody, which makes it possible to construct a molecule model of a substance that blocks the pit of the antibody epitope portion. The antibody fragment of the present invention can be constructed by conventional methods, based on the base sequence information of a DNA that encodes an H chain variable region shown by Seq. ID No. 3 or a DNA that encodes an L chain variable region shown by Seq. ID No. 5, or the amino acid sequence information of an H chain variable region shown by Seq. ID No. 4 or an L chain variable region shown by Seq. ID No. 6.

As to the hybridoma cell line that produces the pemphigus monoclonal antibody of the present invention or a cell line derived from the hybridoma cell line, there is no particular limitation as long as it is a cell line that can produce a monoclonal antibody having a pathological activity capable of inducing pemphigus lesions. The pemphigus monoclonal antibody-producing hybridoma cell line can be generated, for example, by cell fusion of the splenocytes of an animal (preferably an animal aside from human) that produces antibodies against Dsg3 proteins existing in PV mouse model and the myeloma cells derived from the animal by conventional methods, followed by screening the one wherein the monoclonal antibody secreted by the hybridoma can specifically immunoreact against peptide labeled component comprised of amino acid sequence shown in Seq. ID No. 2, from among the hybridoma selected with HAT media. Further, the pemphigus monoclonal antibody of the present invention can be produced by culturing the pemphigus monoclonal antibody-producing hybridoma cell line or a cell line derived from the hybridoma cell line, by conventional methods in vivo or in vitro. For example, the pemphigus monoclonal antibody can be obtained, in an in vivo system, by culturing intraperitoneally in rodent animals such as mouse, rat or the like, preferably in rodent animals wherein its derivation is the same as that of the hybridoma, and in an in vitro system, by culturing in a medium for animal cell cultivation. Examples of a medium for culturing hybridomas in an in vitro system are RPMI1640 containing antibiotics such as streptomycin, penicillin and the like or a medium for cell cultivation such as MEM and the like.

As to the pemphigus autoimmune disease animal model of the present invention, there is no particular limitation as long as it is a non-human animal such as mouse and the like, wherein pemphigus lesions are induced by administering the hybridoma that produces the pemphigus monoclonal antibody of the present invention. For example, when a pemphigus monoclonal antibody-producing hybridoma is injected intraperitoneally into mice or the like, the non-human animal such as mouse and the like is epitope-specifically induced with pemphigus lesions by the pemphigus monoclonal antibody produced by the hybridoma. Screening for a therapeutic drug for pemphigus autoimmune disease can be conducted by the following: administering a test substance to the pemphigus autoimmune disease animal model induced with the pemphigus lesion, and conducting a comparative evaluation with the control of the degree of lesions of pemphigus autoimmune disease such as hair loss,weight loss, suprabasilar acantholysis and the like in the animal model; or by determining the antibody titer in the sera of the animal model by immunoprecipitation, ELISA or the like and conducting a comparative evaluation with the control. There is no particular limitation to the method of administration mentioned above, however, intravenous injection and oral administration can be given as examples.

As to the method for screening the therapeutic drug for pemphigus autoimmune disease of the present invention, aside from the method using the pemphigus autoimmune disease animal model mentioned above, a method wherein the pemphigus monoclonal antibody of the present invention or the antibody fragment of the present invention is reacted with a test substance to conduct a comparative evaluation of the antibody titer in vivo and/or in vitro with a control, or a method wherein the degree of lesion of the pemphigus autoimmune disease compared with the control is evaluated can be given as examples. Examples of method for evaluation in vivo are: a method wherein an antibody or antibody fragment is reacted with a test substance beforehand and administered to a non-human animal such as mouse and the like, or an antibody or antibody fragment and a test substance are administered to a non-human animal such as mouse and the like in random order and reacted in vivo, then the antibody titer in the sera is determined by immunoprecipitation or ELISA; or a method wherein the degree of lesions of the pemphigus autoimmune disease is compared with a control and evaluated. An example of method for evaluation in vitro is a method wherein an antibody or antibody fragment is reacted with a test substance in vitro, and the antibody titer is determined by immunoprecipitation or ELISA, the compared and evaluated with a control.

As to the peptide of the present invention, there is no particular limitation as long as it is a peptide that includes the epitope specifically recognized by the monoclonal antibody of the present invention mentioned above. A pemphigus monoclonal antibody that is a peptide including multiple specific amino acid residues in the amino acid sequence shown by Seq. ID No. 1 or 2, for example, at least one of the valine residue at position 3, lysine residue at position 7 and proline residue at position 8, and an aspartic acid residue at position 59 of Seq. ID No. 1 or 2, and having a pathological activity that can induce pemphigus lesions, preferably a monoclonal antibody that specifically binds to human and mouse Dsg 3 and does not show crossreactivity to human and mouse Dsg 1, and a peptide specifically recognized by a monoclonal antibody comprising an H chain having an amino acid sequence shown by Seq. ID No. 4 or an amino acid sequence constructed by adding, deleting or substituting one or more amino acid residue in the amino acid sequence shown by Seq. ID No. 4, and functions as an H chain of anti-human Dsg3 monoclonal Fab antibody, and an L chain having an amino acid sequence shown by Seq. ID No. 6 or an amino acid sequence constructed by adding, deleting or substituting one or more amino acid residue in the amino acid sequence shown by Seq. ID No. 6, and functions as an L chain of anti-human Dsg3 monoclonal Fab antibody. Further, as the relationship between the antibody that specifically recognizes Dsg3 and the epitope on the Dsg3 molecule is generally common to Dsg1 as well, a peptide corresponding to the Dsg3 epitope mentioned above of Dsg1 can be given as an example. The peptide of the present invention is typically a synthesized peptide, and these peptides can be generated by conventional methods, based on its amino acid sequence information or the base sequence information of the DNA encoding the peptide. Among these peptides of the present invention, the peptides useful as a therapeutic drug that can significantly improve the pathophysiology of the pemphigus is particularly preferable.

As the peptides of the present invention mentioned above are thought to be an epitope of the pemphigus monoclonal antibody having a pathological activity capable of inducing pemphigus lesions such as AK23 mentioned above and the like, those that contain the peptide of the present invention as an active ingredient are useful as a diagnostic drug for pemphigus and a therapeutic drug/preventive drug for pemphigus. ELISA score, which gives an absolute evaluation of the rate at which the disease is progressing, can be obtained if a single epitope ELISA that can determine the antibody titer against a single epitope using the peptide epitope of the present invention can be constructed. It will contribute greatly to the diagnosis for pemphigus such as the severity assessment and the like. Further, by specifically eliminating the autoantibody against this epitope, or by specifically eliminating the B cells that produce the antibody, development of a therapeutic method that is effective to severe pemphigus is expected. The preventive/therapeutic drug for pemphigus of the present invention mentioned above can be added with various compound ingredients for dispensing, such as a pharmaceutically acceptable typical carrier, a bonding agent, a stabilizing agent, an excipient, a diluent, a pH buffer agent, a disintegrant, a solubilizer, a dissolution coadjuvant, an isotonic agent and the like. Further, these preventive or therapeutic drugs can be administered orally or parenterally. In other words, oral administration can be conducted by ordinary administering formulations such as dosage forms of powders, granules, capsules, syrups, and liquid suspension, or parenteral administration can be conducted by injecting the formulations of solution, emulsion, liquid suspension and the like, or it can be further administered through the nostril by the formulation of a spray agent.

Further, the peptide of the present invention can be used as an active ingredient of functional food material or food for the preventive/therapeutic drug of pemphigus autoimmune disease. Examples of the food material or food are: various beverages such as yogurt, yogurt drink, juice, cowmilk, soymilk, alcoholic beverage, coffee, tea, natural leaf tea, oolong tea, isotonic drink, etc.; bread and confectioneries such as baked goods, e.g. pudding, cookies, bread, cake, jelly, rice cracker, Japanese confectioneries, e.g. sweet jellied adzuki-bean pastes, frozen dessert, chewing gum, etc.; noodles such as Japanese wheat noodle, buckwheat noodle, etc.; fish paste products such as steamed fish paste, ham, fish meat sausage, etc.; dairy products such as cheese, butter, etc.; seasonings such as soybean paste, soy sauce, dressing, mayonnaise, sweetener, etc.; bean-curds; devil's tongue; various prepared food such as fish boiled in soy sauce, dumpling, croquette, salad, etc.

The present invention will be described further in more detail with the following examples, however, the technical scope of the invention is not limited to these examples.

EXAMPLE A

Method and Material

A-1 (Construction of rDsg3 Antigen Protein and ELISA)

The baculovirus vectors, pEVmod-Dsg3-His and pEVmod-Dsg1-His, pEVmod-mouse Dsg3-His and pEVmod-mouse Dsg1 -His, that were constructed according to the method as described previously (J. Immunol. 159, 2010-2017, 1997) were used. These recombinant baculoviruses were infected to insect cells, High Five (Invitrogen Corporation), then the recombinant protein human Dsg3-His and Dsg1-His, recombinant protein mouse Dsg3-His and Dsg1-His were collected from the culture media, respectively. In addition, purification of these recombinant proteins was conducted using Ni-NTA column. These purified recombinant proteins were coated on ELISA (Enzyme Linked Immunosorbent Assay) plates, respectively, 50 μl each of the culture supernatant of the anti-Dsg3 monoclonal antibody-producing hybridoma was added to each well, and ELISA was practiced according to the method as previously described (J Clin Invest 105, 625-631, 2000). PV mouse model 1 serum with moderate degree of antibody titer was selected as a positive control, and 1 serum of normal mouse serum was selected as a negative control. Absorbance was determined at wavelength 450 nm (Bio-rad, Hercules, Calif. USA), and the index was shown by the following formula.

Index={$OD$(specimen)−$OD$(negative control)}/{$OD$(positive control)−$OD$(negative control)}×100

A-2 (Living Cell Staining Using Culture Mouse Keratinocyte PAM 212)

Culture mouse keratinocyte PAM 212 (Cancer Research 40, 4694-4703, 1980) were cultured in 8 wells of Chamber slide (Nalge Nunc International, USA). The culture solution was substituted to 30-fold diluted PV mouse model serum or hybridoma culture supernatant, and the cells were cultured in 5% $CO_2$ incubator for 30 minutes at 37° C. After the cells were washed with PBS on ice (3 times), 100% methanol was added, and they were fixed for 20 minutes at −20° C. After the cells were washed with PBS (3 times), 100-fold diluted FITC labeled goat anti-mouse IgG (DAKO A/S, Glostrup, Denmark) was added, and after reaction for 30 minutes at room temperature, then they were washed with PBS (3 times), and microscopic examination was conducted using a fluorescence microscope (Eclipse E800, NIKON Corp. Tokyo, Japan).

A-3 (Construction of PV Model Mice)

Mice having genetic background of 129/SV (H-$2^b$) and C57BL/6J (H-$2^b$) were used for Dsg3 knockout (−/−) mice (The Jackson laboratory, Bar Harbor, Mane, USA). Mice that were backcrossed for 10 generations to B6.SJL-ptpr$^c$ were used for Rag (Recombinase activating gene) $2^{-/-}$ mice (Taconic Farms, Germantown, N.Y. USA) used as recipient mice (Shinkai, Y. et al.: RAG-2 deficient mice lack mature lymphocytes owing to inability to initiate V (D) J rearrangement. Cell, 68: 855-867, 1992). Dsg3$^{-/-}$ mice were immunized primarily with recombinant mouse Dsg3-His (5 μg/mouse) in complete Freund's adjuvant subcutaneously. 7 and 14 days after the primary immunization, recombinant mouse Dsg3-His (5 μg/mouse) and incomplete Freund's adjuvant were injected intraperitoneally. 21 days after the primary immunization and 4 days before transfer of mouse splenocytes, the recombinant mouse Dsg3-His (5 μg/mouse) alone was injected intraperitoneally for immunization. 1×$10^7$ of Dsg3$^{-/-}$ mouse splenocytes were suspended in 500 μl PBS (Phosphate Buffered Saline), and then intravenously injected through the tail vein of Rag2$^{-/-}$ mice. 30 days after the transfer of splenocyte, hair loss and serologically collected the recipient mice sera, and the production of anti-mouse Dsg3 antibody was confirmed by ELISA with mouse Dsg3-His as an antigen and living cell staining.

A-4 (Construction of Monoclonal Antibody)

The splenocytes of PV mouse models having a gross phenotype with anti-Dsg3 antibody and the mouse myeloma cell line P3 were adjusted to 1:5, and cell fusion was conducted with polyethylene glycol 4000. After the cell fusion, 1×$10^7$ cells per plate were suspended in HAT (hypoxanthine aminopterin thymidine) medium-10% HCF (hybridoma cloning factor) (IGEN International, Inc., Gaithersburg, Md., USA) and dispensed at 100 μl/well in a 96 well flat-bottomed plate. The cells were cultured for 10 to 14 days in 5% $CO_2$ incubator at 37° C. 50 μl of the culture supernatant was collected from colony positive wells, and primary screening was conducted by ELISA using mouse Dsg3. The primary screening positive hybridomas were subjected to secondary screening by living cell staining using mouse keratinocyte cell line, PAM212. Positive clones were cultured in a 24 well plate with HT (hypoxanthine thymidine) medium-5% HCF. Ultimately, the culture media was changed to RPMI 1640 medium-10% fetal bovine serum (FBS) (Hyclone, Utah, USA). These hybridomas were adjusted to 1 cell per well in a 96 well plate (Coaster, N.Y., USA), and cultured in 5% $CO_2$ incubator at 37° C. 10 to 14 days later, the culture supernatant of colony positive wells were screened by ELISA and living cell staining using mouse Dsg3, cloning was conducted for a total of 3 times, and monoclonal antibody-producing hybridomas were established. The isotypes were determined by using a mouse monoclonal antibody isotyping kit (Iso Storip, Roche, Mannheim, Germany).

A-5 (Indirect Immunofluorescence)

C57Bl/6J mouse hard palate, liver and human skin were embedded with OCT compound (SAKURA, USA), then froze and sectioned into 5 μm thickness, and constructed a substrate. After each of hybridoma culture supernatants were reacted for 1 hour at room temperature, they were washed with PBS (3 times), and reacted with ×100 diluted FITC labeled goat anti-mouse IgG (DAKO A/S, Glostrup, Denmark) for 1 hour at room temperature, they were washed with PBS (3 times), and microscopic examination was conducted using a fluorescence microscope.

A-6 (Immunoprecipitation and Immunoblotting)

200 μl of each monoclonal antibody-producing hybridoma culture supernatant and 20 μg of the mouse Dsg3-His were mixed, then stirred and reacted for 1 hour at room temperature. Then 10 μl of protein G (Protein G sepharose 4 fast flow: Amersham Pharmacia Biotech, Buckinghamshire, England) was added and reacted overnight at 37° C. Centrifugation was conducted after the reaction, and 50 μl of SDS was added to the precipitate and boiled for 2 minutes. Each sample was subjected to electrophoresis with a 7.5% uniform gel plate for electrophoresis (multigel 7.5: Daiichi Pure Chemicals, Tokyo, Japan), transcribed to PVDF membrane, then blocked. Further, 100-fold diluted anti-6X histidine antibody (R&D systems, Inc. Minn., USA) was reacted for 1 hour at room temperature, washed (3 times) in TBS (Tris buffered saline), then 1000-fold diluted alkaline phosphatase-goat anti-mouse IgG (Zymed, San Francisco, Calif., USA) was reacted for 1 hour at room temperature, washed (3 times) in TBS, then developed.

A-7 (Purification of Monoclonal Antibody)

Mass culture of hybridomas was conducted in RPMI1640 culture solution, and the culture supernatant was concentrated and purified in protein A column as follows: 3 M of NaCl and 50 mM of Tris-HCl (pH 8.0) were added to the culture supernatant, centrifugation was conducted, and followed by filtration with a 0.45 μm filter. The antibodies were bonded in a column filled with 5 ml of recombinant Protein A (HiTrap rProteinA FF: Amersham Pharmacia Biotech, Buckinghamshire, England), the column was washed in 50 mMTris-HCl (pH 8.0) including 3 MNaCl, then followed by extraction in 1

M $CH_3COONa$ (pH 5.0). After the extraction, the buffer solution was replaced with PBS in a desalt column, HiTrap Desalting (Amersham Pharmacia Biotech, Buckinghamshire, England), and protein concentration was determined by OD280 (1.4OD=1 mg/ml).

A-8 (Concentration of the Serum of Patient with Pemphigus Foliaceus)

1 patient sera clinically and histopathologically having the characteristic of pemphigus foliaceus (PF) and serologically having a diagnosis of PF by indirect immunofluorescence and ELISA was selected. Protein of the patient sera was precipitated in 40% saturated ammonium sulfate (SAS), the precipitated solution was dissolved in PBS after centrifugation, and the buffer solution was replaced in 100-fold volume of PBS (3 times). Further, the solution was concentrated to 10-fold concentration (20 mg/ml) in Centriprep (Millipore, Mass., USA).

A-9 (Confirmation of the Pathogenicity of Monoclonal Antibody)

Confirmation of the pathogenicity of monoclonal antibody was conducted by passive transfer of antibodies to neonatal mice and inoculation of hybridomas to $Rag2^{-/-}$ immunodeficient mice. First, the PF patient sera (20 mg/ml) that was simultaneously transferred with the monoclonal antibody was transferred alone for 5 μl, 10 μl and 20 μl, and the amount wherein gross and histopathological blister formation is not found was determined. In the same manner, ETA (exfoliative toxin A) was used (Nature Medicine 6, 1275-1277, 2000), and the amount wherein lesion is not induced by its use alone was determined. Passive transfer to neonatal mice was conducted in 3 types of combinations, that is, monoclonal antibody alone (30 to 300 μg/150 μl/mouse), simultaneous transfer (total of 150 μl/mouse) of monoclonal antibody and PF patient sera in the amount that does not induce lesions (1 mg/5 μl/mouse) by itself, and monoclonal antibody and ETA in the amount that does not induce lesions by itself (total of 150 μl/mouse). 150 μl of prepared solution was subcutaneously injected with an insulin syringe pump between scapulas of neonatal mice (ICR; Sankyo labo service, Tokyo, Japan) within 24 hours from birth and having body weight of 1.6 to 1.8 g. 18 to 24 hours after the injection, the mice were decapitated and tissues were collected. Sections of the skin and head were fixed with 10% PBS buffer formalin for histopathological examination. Histopathologically, the number of pathological sections constructed per mouse collected and number of blister formation in the section (fragments, sequential parts) were counted. $Rag2^{-/-}$ immunodeficient mice were used to confirm the pathogenicity. 500 μl of pristane (2, 6, 10, 14-Tetramethyl-pentadecane, Wako, Osaka, Japan) were intraperitoneally injected into $Rag2^{-/-}$ mice of 4-week old or older, and 1 week later, more than $1 \times 10^7$ hybridoma cells were inoculated. 7 to 10 days after the inoculation, the presence of hair loss, immunohistologically, the deposition of antibodies at the palatal mucous membrane and plantar skin were studied by direct immunofluorescence, and histopathologically, blister formation at the palate portion were studied.

A-10 (Direct Immunofluorescence)

The skin and head tissue sections of neonatal mice were embedded with OCT compound, then froze and thin sections of 5 μm thickness were constructed. After 100-fold diluted FITC labeled goat anti-mouse IgG (DAKO A/S, Glostrup, Denmark) were reacted for 60 minutes at room temperature, they were washed with PBS (3 times), and microscopic examination was conducted using a fluorescence microscope.

A-11 (Construction of Domain-swapped Molecules with Dsg1 and Dsg3)

Figure 4:
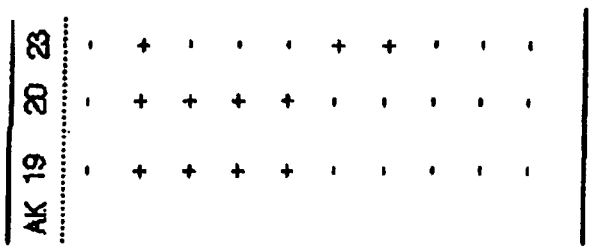
FIG. 4 is a view showing the structure of the Dsg domain-swapped molecules, and the reactivity of these swapped molecules and anti-Dsg3 monoclonal antibody of the present invention examined by immunoprecipitation.
Figure 4:
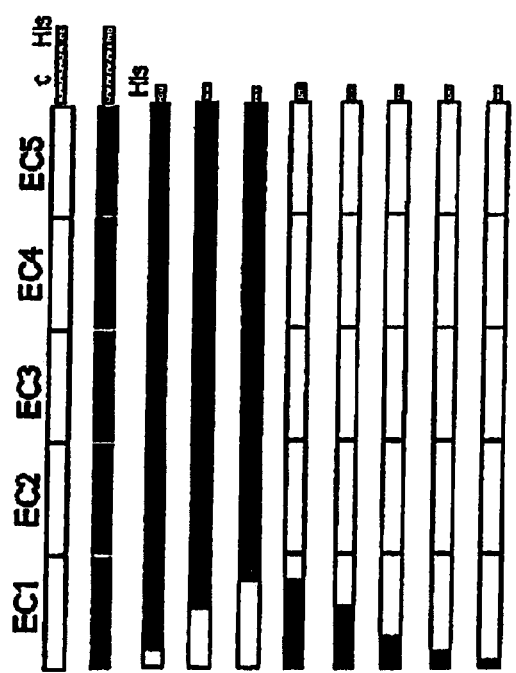

8 types of domain-swapped molecules of human Dsg3 and human Dsg1 were constructed in order to analyze the epitope on Dsg3 molecules of the monoclonal antibody, by the method wherein the extracellular domain of Dsg1 or Dsg3 is substituted to the respectively corresponding Dsg3 or Dsg1 region. Among these, 5 types of the domain-swapped molecules have a Dsg3 fragment at the N terminal region ($Dsg3^{1-88}/Dsg1^{89-496}$, $Dsg3^{1-63}/Dsg1^{63-496}$, $Dsg3^{1-34}/Dsg1^{35-496}$, $Dsg3^{1-26}/Dsg1^{26-496}$, $Dsg3^{1-10}/Dsg1^{11-496}$), and 3 types have a Dsg1 fragment at the N terminal region ($Dsg1^{1-87}/Dsg3^{87-566}$, $Dsg1^{1-64}/Dsg3^{65-566}$, $Dsg1^{1-24}/Dsg3^{25-566}$). pEVmod-PVIg (GenBank Accession No. M76482) (J. Clin. Invest. 94, 59, 1994) and pKS-Dsg1 (GenBank Accession No. X56654) were used as templates, respectively, and the cDNA for the various regions of Dsg1 and Dsg3 were amplified by PCR using the primers shown in Table 1 (primers 1 to 22, having a base sequence shown by Seq. ID Nos. 7 to 28). In order to narrow down the epitope of autoantibody, 8 types of domain-swapped chimeric constructs containing His tags at the C terminal were constructed, respectively (FIG. 4).

The PCR product of Dsg1 fragment comprising residues 1-87, 1-64/1-24, 89-496/63-496/26-496/35-496, 11-496 was digested with BglII/AatII, BglII/SpeI, AatII/SalI, SpeI/SalI, NcoI/XhoI, respectively. The PCR product of Dsg3 fragment comprising residues 1-88, 1-63/1-10, 1-34/1-26, 87-566/65-566/25-566 was digested with BglII/AatII, BglII/SpeI, NcoI/EcoRI, AatII/XhoI, SpeI/XhoI, respectively. The product obtained thereby was digested with BglII/XhoI, then ligated into an expression vector pEVmod-His (J. Immunol. 159, 2010, 1997) ($Dsg3^{1-88}/Dsg1^{89-496}$, $Dsg3^{1-63}/Dsg1^{63-496}$, $Dsg3^{1-26}/Dsg1^{26-496}$, $Dsg1^{1-87}/Dsg3^{87-566}$, $Dsg1^{1-64}/Dsg3^{65-566}$, $Dsg1^{1-24}/Dsg3^{25-566}$). In addition, the product obtained thereby was ligated into an expression vector pQE vector (QIAGEN, Hilden, Germany) ($Dsg3^{1-34}/Dsg1^{35-496}$, $Dsg3^{1-10}/Dsg1^{11-496}$). The domain swapped-chimeric constructs introduced into these expression vectors were expressed as a secretory protein by the baculovirus expression system, and a domain-swapped molecule was produced.

TABLE 1

Primers used for domain swapped human Dsg molecules

| Constructs | Primers for hDsg1 | | Primers for hDsg3 | |
|---|---|---|---|---|
| | 5' primers | 3' primers | 5' primers | 3' primers |
| $Dsg1^{1-24}/Dsg3^{25-566}$ | primer 1 | primer 2 | primer 3 | primer 4 |
| $Dsg1^{1-64}/Dsg3^{65-566}$ | primer 1 | primer 5 | primer 6 | primer 4 |
| $Dsg1^{1-87}/Dsg3^{87-566}$ | primer 1 | primer 7 | primer 8 | primer 4 |
| $hDsg3^{1-10}/hDsg1^{11-496}$ | primer 9 | primer 10 | primer 11 | primer 12 |

TABLE 1-continued

Primers used for domain swapped human Dsg molecules

|  | Primers for hDsg1 | | Primers for hDsg3 | |
|---|---|---|---|---|
| Constructs | 5' primers | 3' primers | 5' primers | 3' primers |
| Dsg3$^{1-26}$/Dsg1$^{26-496}$ | primer 13 | primer 14 | primer 15 | primer 16 |
| hDsg3$^{1-34}$/hDsg1$^{35-496}$ | primer 17 | primer 10 | primer 11 | primer 18 |
| Dsg3$^{1-63}$/Dsg1$^{63-496}$ | primer 19 | primer 14 | primer 15 | primer 20 |
| Dsg3$^{1-88}$/Dsg1$^{89-496}$ | primer 21 | primer 14 | primer 15 | primer 22 |

Primer 1: 5'-gaagatctcctataaatatggactggagtttcttcagag-3'
(SEQ ID NO. 7)
Primer 2: 5'-cggactagtaattttggcgattgggtt-3'
(SEQ ID NO. 8)
Primer 3: 5'-gccactagtgattaccaagcaacccag-3'
(SEQ ID NO. 9)
Primer 4: 5'-cctgctcgagcctccctgagtgcggcct-3'
(SEQ ID NO. 10)
Primer 5: 5'-cggactagttatattaatttcaccagt-3'
(SEQ ID NO. 11)
Primer 6: 5'-gccactagtatagtcgaccgggaggaa-3'
(SEQ ID NO. 12)
Primer 7: 5'-cgggacgtcttggcccattgagttcag-3'
(SEQ ID NO. 13)
Primer 8: 5'-gccgacgtcgagaaaccacttatacta-3'
(SEQ ID NO. 14)
Primer 9: 5'-ctggtttgcagcacaatctgagtgaatcttggcaattgggtttctttt-3'
(SEQ ID NO. 15)
Primer 10: 5'-ttactgccatccagttagctgaga-3'
(SEQ ID NO. 16)
Primer 11: 5'-gacaaccatgggctcttcccagaactac-3'
(SEQ ID NO. 17)
Primer 12: 5'-ttgccaaaccctgcagaatcaagttcgcagcagcctgtcgt-3'
(SEQ ID NO. 18)
Primer 13: 5'-gccactagtgattgtgctgcaaaccag-3'
(SEQ ID NO. 19)
Primer 14: 5'-cttgtcgacatgtacattgtctgataacaaatc-3'
(SEQ ID NO. 20)
Primer 15: 5'-gaagatctcctataaatatggggctcttcccag-3'
(SEQ ID NO. 21)
Primer 16: 5'-cggactagtaatcttggcaattgggtt-3'
(SEQ ID NO. 22)
Primer 17: 5'-ccaagcaacccagaaaatcacataccgcatctctggagta-3'
(SEQ ID NO. 23)
Primer 18: 5'-tgctgcgaacttgattctgcagggtttggcaaatttcaccca-3'
(SEQ ID NO. 24)
Primer 19: 5'-gccactagtatagttgatcgagaggtc-3'
(SEQ ID NO. 25)
Primer 20: 5'-cggactagttatgttaatatctccagt-3'
(SEQ ID NO. 26)
Primer 21: 5'-gccgacgtcgagaggcctctagagctc-3'
(SEQ ID NO. 27)
Primer 22: 5'-cgggacgtctagtccttgggcatttag-3'
(SEQ ID NO. 28)

A-12 (Construction of Point-mutated Molecules)

Figure 5:
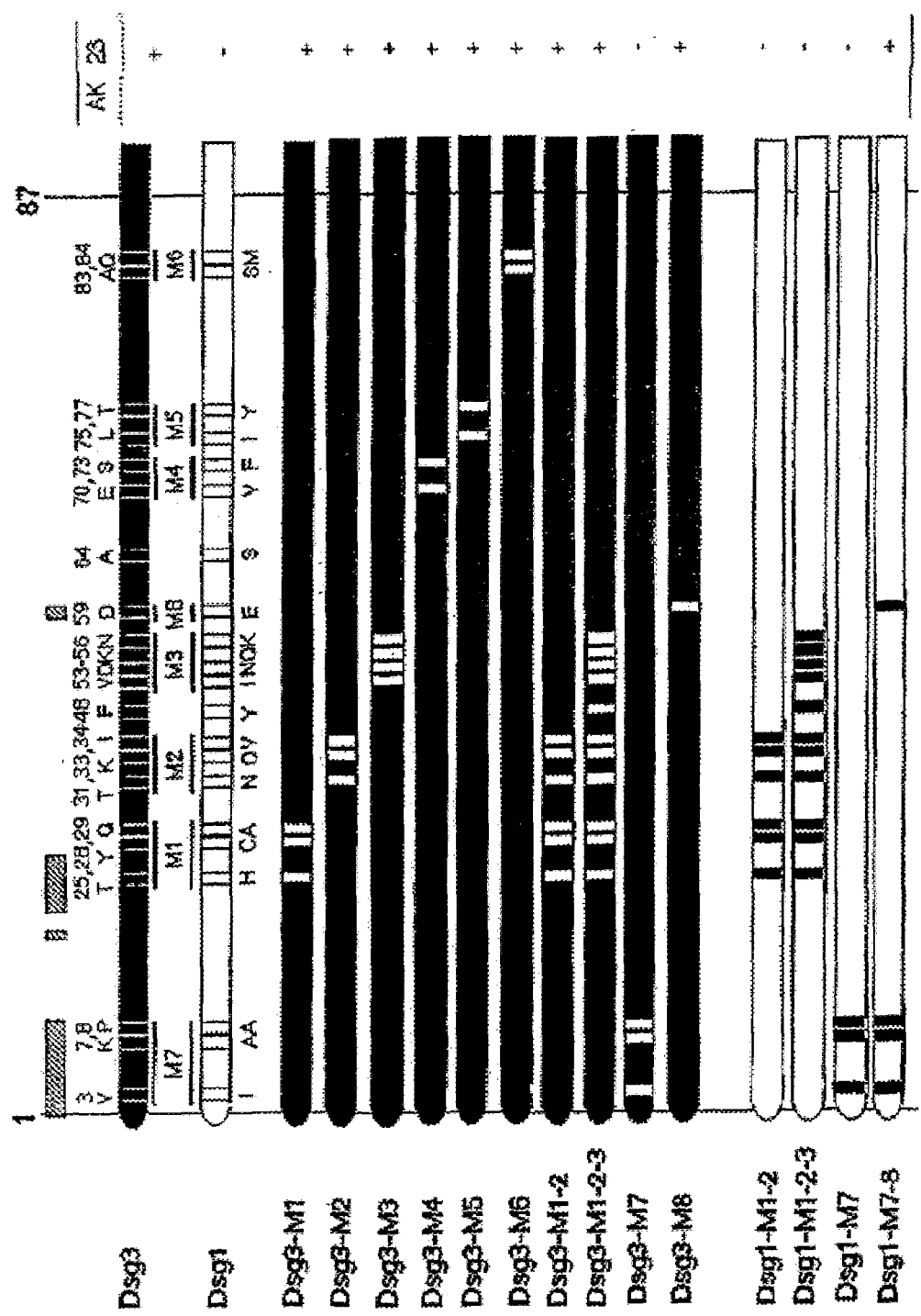
FIG. 5 is a view showing the structure of the Dsg point-mutated molecules, and the reactivity of these point-mutated molecules and the anti-Dsg3 monoclonal antibody of the present invention examined by immunoprecipitation.

Further, 14 types of point-mutated molecules wherein the amino acid at the amino terminal 1-87 region of Dsg3 and Dsg1 were substituted, in order to analyze the AK23 epitope in more detail. 10 types of the point-mutated molecules among them are those wherein the Dsg3-specific amino acid in the Dsg3 molecule is substituted to a Dsg1-specific amino acid (Dsg3-M1, Dsg3-M2, Dsg3-M3, Dsg3-M4, Dsg3-M5, Dsg3-M6, Dsg3-M7, Dsg3-M8, Dsg3-M1-2, Dsg3-M1-2-3), and 4 types among them are those wherein the Dsg1-specific amino acid in the Dsg1 molecule is substituted to a Dsg3-specific amino acid (Dsg1-M1-2, Dsg1-M1-2-3, Dsg1-M7, Dsg1-M7-8) (FIG. 5). Further, in order to introduce the point mutation, for the 6 types of Dsg3-M1 to M6 mentioned above, site-directed mutagenesis treatment was conducted according to the unique restriction site elimination method (Anal. Biochem. 200, 81, 1992) and megaprimer method based on PCR (Barik, S. Site-directed mutagenesis by double polymerase chain reaction. In PCR protocols, vol. 15, B. A. White, ed. Humana Press, Totowa, p. 277, 1993). Further, for the 8 remaining types, site-directed mutagenesis treatment was conducted by two-step PCR method (J Invest Dermatol. 107, 539-542, 1996).

In order to conduct these treatments, 26 mutated primers shown in Table 2 (primers 23 to 48, each having a base sequence shown by Seq. ID Nos. 29 to 54) were constructed. For the 6 types of Dsg3-M1 to M6, a mutagen primer (5'-GACTTGGTTGAATACTCACCAG-3'; Seq. ID No. 55) and a plasmid template (pEVmod-Dsg3-His) that encodes the extracellular domain of Dsg3) were used to construct a megaprimer containing a mutation by primary PCR. By conducting this treatment, the unique ScaI restriction site (AATACT) in the amp$^r$ gene was eliminated (Anal. Biochem. 200, 81, 1992). In the PCR for the second time, the megaprimer was used with the same plasmid template in order to amplify the total plasmid. After the DpnI digestion, the PCR product was used for conversion. All mutants were subjected to sequencing, and it was confirmed whether mutants existed, as well as whether other mutants were introduced. Each of the PCR products mentioned above were digested with BglII/XhoI, and ligated with an expression vector pEVmod-His (J. Immunol. 159, 2010, 1997). Further, for the remaining 8 types, the PCR product of Dsg1 fragment was digested with NcoI/XhoI, the PCR product of Dsg3 fragment was digested with NcoI/EcoRI, then ligated into an expression vector pQE vector (QIAGEN, Hilden, Germany). The point-mutated DNA constructs introduced into these expression vectors were expressed as a secretory protein in the baculovirus expression system, and point-mutated molecules were constructed.

TABLE 2

Primers used for point-mutated human Dsg1/Dsg3 molecules

| Constructs | Primers | Amino Acid Change |
|---|---|---|
| Dsg3-M1 | 23 | T25H, Y28C, Q29A |
| Dsg3-M2 | 24 | T31N, K33Q, I34V |
| Dsg3-M3 | 25 | V53I, D54N, K55Q, N56K |
| Dsg3-M4 | 26 | E70V, S73F |
| Dsg3-M5 | 27 | L75I, T77Y |
| Dsg3-M6 | 28 | A83S, Q84M |
| hDsg3-M1-2 | 29, 31, 33, 34 | T25H, Y28C, Q29A, T31N, K33Q, I34V |
| hDsg3-M1-2-3 | 29, 31, 35, 36 | T25H, Y28C, Q29A, T31N, K33Q, I34V |
| | | F48Y, V53I, D54N, K55Q, N56K |
| hDsg3-M7 | 29, 31, 41, 42 | V3I, K7A, P8A |
| hDsg3-M8 | 29, 31, 43, 44 | D59E |
| hDsg1-M1-2 | 30, 32, 37, 38 | H25T, C28Y, A29Q, N31T, Q33K, V34I |
| hDsg1-M1-2-3 | 30, 32, 39, 40 | Y48F, I53V, N54D, Q55K, K56N |
| hDsg1-M7 | 30, 31, 32, 45 | I3V, A7K, A8P |
| hDsg1-M7-8 | 30, 32, 45, 46, 47, 48 | I3V, A7K, A8P, E59D |

Primer 23:
5'-gaaacccaattgccaagattcattcagattgcgcagcaacccagaaaatcacctac-3'
(SEQ ID NO. 29)
Primer 24:
5'-acttcagattaccaagcaaaccagcaagtcacctaccgaatctctggag-3'
(SEQ ID NO. 30)
Primer 25:
5'-ggccgccttttggaatctttgttattaaccaaaaaactggagatattaacataacag-3'
(SEQ ID NO. 31)
Primer 26:
5'-gctatagtcgaccgggaggtaactccattcttcctgatcacatgtcgg-3'
(SEQ ID NO. 32)
Primer 27:
5'-gaggaaactccaagcttcatcatctattgtcgggctctaaatgcc-3'
(SEQ ID NO. 33)
Primer 28:
5'-catgtcgggctctaaatagcatgggactagatgtagag-3'
(SEQ ID NO. 34)
Primer 29:
5'-gacaaccatggggctcttccccagaactac-3'
(SEQ ID NO. 35)
Primer 30:
5'-gcagccatggactggagtttcttcagagta-3'
(SEQ ID NO. 36)
Primer 31:
5'-cggactagtgaggaacatgggtgtgccagc-3'
(SEQ ID NO. 37)
Primer 32:

TABLE 2-continued Primers used for point-mutated human Dsg1/Dsg3 molecules

| Constructs | Primers | Amino Acid Change |
|---|---|---|

5'-ttactgccatccagttagctgaga-3'
(SEQ ID NO. 38)
Primer 33:
5'-ctggtttgcagcacaatctgagtgaatcttggcaattgggtttctttt-3'
(SEQ ID NO. 39)
Primer 34:
5'-gattgtgctgcaaaccagcaagttacctaccgaatctctggagtggga-3'
(SEQ ID NO. 40)
Primer 35:
5'-atcaattcctactccagagatgcggtat-
gtaacttgctggtttgcagcacaatctgagtgaatcttggcaattgggtttcttttgag3'
(SEQ ID NO. 41)
Primer 36:
5'-cgcatctctggagtaggaattgatcagc-
caccatatgggatctttgtcattaatcagaaaactggagatattaacataacagcta-3'
(SEQ ID NO. 42)
Primer 37:
5'-ctgggttgcttggtaatctgaagtaattttggcgattgggttcctctt-3'
(SEQ ID NO. 43)
Primer 38:
5'-gattaccaagcaacccagaaaatctaccgcatctctggagtaggaattg-3'
(SEQ ID NO. 44)
Primer 39:
5'-atcgattcccactccagagattcggtag-
gtgattttctgggttgcttggtaatctgaagtaattttggcgattgggttcctctttga-3'
(SEQ ID NO. 45)
Primer 40:
5'-cgaatctctggagtgggaatcgatcagc-
cgccttttggaatctttgttgttgacaaaaacactggtgaaattaatataacatccatag-3'
(SEQ ID NO. 46)
Primer 41:
5'-cttctctgcaggcagcggcaaatttgatccattcacgttt-3'
(SEQ ID NO. 47)
Primer 42:
5'-tgaatggatcaaatttgccgctgcctgcagagaaggagaa-3'
(SEQ ID NO. 48)
Primer 43:
5'-aaaaacactggagaaattaacataacagc-3'
(SEQ ID NO. 49)
Primer 44:
5'-tgttatgttaatttctccagtgttttgtc-3'
(SEQ ID NO. 50)
Primer 45:
5'-tgaatgggtgaagttcgcaaaaccctgtcgtgaaggtgaa-3'
(SEQ ID NO. 51)
Primer 46:
5'-cttcacgacagggttttgcgaacttcacccattcacgttt-3'
(SEQ ID NO. 52)
Primer 47:
5'-aaactggtgatattaatataacatcc-3'
(SEQ ID NO. 53)
Primer 48:
5'-atattaatatcaccagttttctgatt-3'
(SEQ ID NO. 54)

EXAMPLE B

Results

B-1 (Reactivity of Monoclonal Antibodies)

The PV mouse model with an active disease can induce loss of cell-cell adhesion of keratinocytes, thereby having a circulating anti-Dsg3 IgG antibody that forms blisters. The present inventors used this PV mouse model as a supply source for developing anti-Dsg3 IgG monoclonal antibody. The present inventors produced hybridoma cells from the splenocytes of these mice. First, for these hybridoma cells, recombinant Dsg3 obtained from the baculovirus expression system were used for screening with ELISA, and for positive clones, screening was further performed by living keratinocyte staining using mice keratinocyte PAM212 cells (FIGS. 1a, 1b and 1c). In the screening for the second time, antibodies capable of binding to native Dsg3 at the surface of keratinocytes in vivo were selected, and 8 different clones were isolated (Table 3). The isotypes of these monoclonal antibodies were all IgG1 for H chain and K for L chain.

ELISA method using recombinant Dsg protein as an antigen, indirect immunofluorescence using each organ of mice as a substrate, and living cell staining using culture mouse keratinocyte PAM212 cells were conducted to examine the antigen specificity of the monoclonal antibodies. Indirect immunofluorescence showed that all of these antibodies reacted with cell surfaces of stratified squamous epithelia such as hard palate or skin, but not with simple epithelia such as liver or intestine. Further, the staining patterns of these monoclonal antibodies were indistinguishable from those of mouse sera from PV model mice or PV patients sera. Some monoclonal antibodies (AK 1, 15, 18, 19, 20 and 23) cross-reacted with human skin or mucosa. These antibodies stained entire layers in mucosa and lower layers in human epidermis where Dsg3 is expressed (FIGS. 1*d*, 1*e*, 1*f*). All of the antibodies exclusively reacted with the recombinant extracellular domain of mouse Dsg3 by ELISA except AK1 which cross-reacted with mouse Dsg1. The ones which showed crossre-activity against human tissues by immunofluorescence also reacted with recombinant human Dsg3 by ELISA. Table 3 mentioned above shows the characteristic of 8 clones which were an IgG1 K. In Table 3, (+) indicates positive and (−) indicates negative in indirect immunofluorescence (IIF) and ELISA, respectively. For calcium dependency, the reactivity of the monoclonal antibodies against mouse Dsg3 was conducted with or without EDTA treatment, and those wherein reactivity is deficient due to EDTA are shown by (+). Further, for epitope, the epitopes of AK7, AK9, AK15, AK18 and AK20 are shown by amino acid residues of mouse Dsg3, and AK19 and AK20 are shown by amino acid residues of human Dsg3.

TABLE 3

Overview of the specificity of AK monoclonal antibodies

| | | IIF | | ELISA | | | |
|---|---|---|---|---|---|---|---|
| | | Mice | | | | | |
| | | Mucous | | Human | Mice | | Human | |
| AK | Isotype | Membrane | Liver | Skin | Dsg3 | Dsg1 | Dsg3 | Dsg1 |
| 1 | IgG1 κ | + | − | + | + | + | + | + |
| 7 | IgG1 κ | + | − | − | + | − | − | − |
| 9 | IgG1 κ | + | − | − | + | − | − | − |
| 15 | IgG1 κ | + | − | + | + | − | + | − |
| 18 | IgG1 κ | + | − | + | + | − | + | − |
| 19 | IgG1 κ | + | − | + | + | − | + | − |
| 20 | IgG1 κ | + | − | + | + | − | + | − |
| 23 | IgG1 κ | + | − | + | + | − | + | − |

| | | Living | Calcium | Pathogenicity | | |
|---|---|---|---|---|---|---|
| AK | Isotype | Keratinocyte Staining | Depen-dency | Passive Transfer | Ascites Formation | Epitope |
| 1 | IgG1 κ | + | − | − | − | ND |
| 7 | IgG1 κ | + | − | − | − | 403-565 |
| 9 | IgG1 κ | + | − | − | − | 403-565 |
| 15 | IgG1 κ | + | − | − | − | 195-402 |
| 18 | IgG1 κ | + | − | − | − | 195-402 |
| 19 | IgG1 κ | + | + | + | − | 87-161 |
| 20 | IgG1 κ | + | − | − | − | 403-565 |
| 23 | IgG1 κ | + | + | + | + | V3, K7, P8, D59 |

As can be seen from Table 3, in indirect immunofluorescence using mouse and human substrates, all the clones are specific to Dsg3, and AK7 and AK9 are specific to mouse Dsg3. In an examination by ELISA mentioned above using various recombinant Dsg proteins as antigens, AK1 was found to have reactivity to all of the Dsgs (Dsg3 and Dsg1 of human and mouse). Further, AK7 and AK9 were found to have reactivity only to mouse Dsg3. AK15, AK18, AK19, AK20 and AK23 were clones having crossreactivity with Dsg3 of mouse and human. AK20 among them showed weak reactivity against human Dsg3, but AK23 showed a significantly strong reactivity against human Dsg3. In living cell staining using culture mouse keratinocytes, all the clones were having reactivity to Dsg3 in vivo. In addition, only AK 19 and AK23 were the clones having sensitivity to calcium. In confirmation of pathogenicity using neonatal mice, blister formation was confirmed in AK19 and AK23. In confirmation of pathogenicity due to the ascites formation in Rag2$^{-/-}$ mice using hybridoma, blister formation was confirmed only in AK23. Based on these results, it was demonstrated that the epitope recognized by the monoclonal antibody constructed is not single.

B-2 (Pathogenicity of monoclonal antibodies in neonatal mice)

All of the monoclonal antibodies were used to confirm the pathogenicity by transfer of monoclonal antibodies to neonatal mice. First, the gross blister formation of the skin of neonatal mice wherein each monoclonal antibody is transferred alone and the microscopic microblister formation were observed in hematoxylin eosin staining. As a result, no gross blister formation was found in all of the monoclonal antibody. Next, microscopic microblister formation was examined. As an examination item, the number of tissue sections in 1 specimen and the number of suprabasilar acantholysis found in the fragment and sequential parts (sequential parts that connect both fragments) were counted. As a result, in mouse transferred with AK23, while the total number of section was 15, the number of microscopic blister formation was 6 for fragment, 4 for sequential part and total 10. In mouse transferred with AK19, while the total number of section was 37, the number of microscopic blister formation was 6 for fragment, 7 for sequential part and total 13. In mouse transferred with other monoclonal antibodies such as AK20, while the total number of section was 18, no microblister formation was observed in either of the fragment and sequential part. Table 4 shows the results of the cases wherein AK19, AK20 and AK23 were used.

TABLE 4

| | Gross | Microscopic blister Formation | | |
|---|---|---|---|---|
| | Blister Formation | Number of Sections | Fragments | Sequential Parts |
| AK23 | | | | |
| AK23-1 | 0 | 6 | 3 | 0 |
| AK23-2 | 0 | 5 | 2 | 3 |
| AK23-3 | 0 | 4 | 1 | 1 |
| subtotal | 0 | 15 | 6 | 4 |
| total | 0 | 15 | 10 | |
| AK19 | | | | |
| AK19-1 | 0 | 8 | 3 | 3 |
| AK19-2 | 0 | 8 | 0 | 0 |
| AK19-3 | 0 | 5 | 3 | 3 |
| AK19-4 | 0 | 5 | 0 | 0 |
| AK19-5 | 0 | 6 | 0 | 0 |
| AK19-6 | 0 | 5 | 0 | 1 |
| subtotal | 0 | 37 | 6 | 7 |
| total | 0 | 37 | 13 | |
| AK20 | | | | |
| AK20-1 | 0 | 4 | 0 | 0 |
| AK20-2 | 0 | 6 | 0 | 0 |
| AK20-3 | 0 | 4 | 0 | 0 |
| AK20-4 | 0 | 4 | 0 | 0 |
| subtotal | 0 | 18 | 0 | 0 |
| total | 0 | 18 | 0 | |

Figure 2:
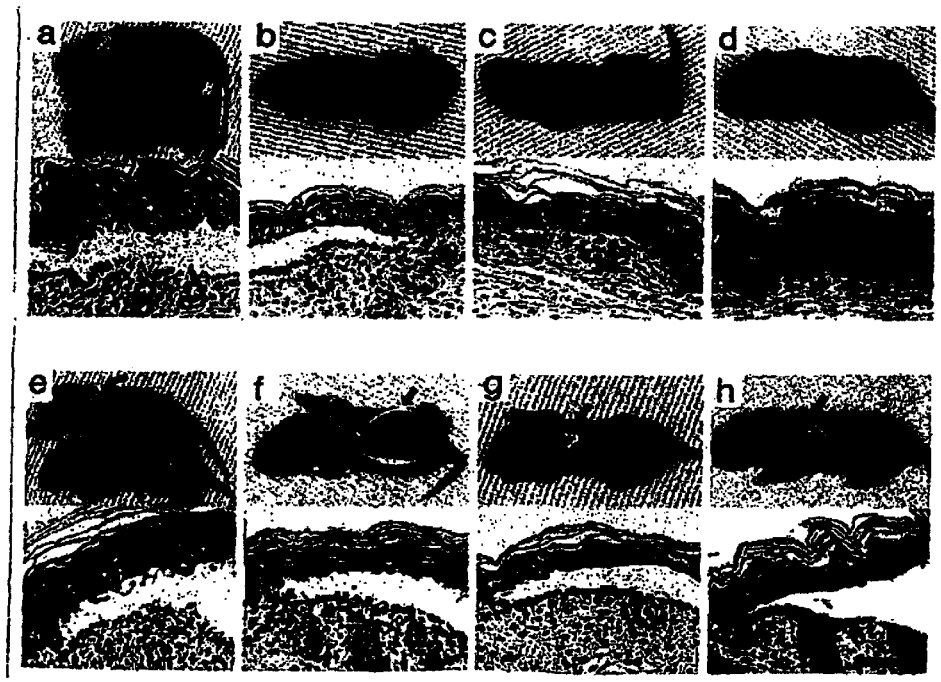
FIG. 2 is a photograph showing the results when the anti-Dsg3 monoclonal antibody of the present invention is passively transferred alone to a neonatal mouse.

Based on the findings mentioned above, passive transfer assay was further conducted mainly to. AK23 and AK19, which are considered as having the pathogenicity (FIG. 2). In transfer alone of AK19 (FIG. 2a) or AK23 (FIG. 2b) into neonatal mice, no apparent gross blister formation was found, however, with the use of microscope, AK19 (FIG. 2c) and AK23 (FIG. 2d) both histopathologically showed PV-specific microscopic blister with suprabasilar acantholysis by hematoxylin eosin staining. It was considered that the reason gross blister formation was not found is because the Dsg1 adhesion function compensates the impaired Dsg3 adhesive function by AK23 or AK19 due to the coexpression of Dsg1 in the skin. A small amount of anti-Dsg1 antibody (PF patient sera) that does not induce apparent blister formation in itself was simultaneously injected, and extensive gross blister formation in neonatal mice was found in both AK19 (FIG. 2e) and AK23 (FIG. 2f), and suprabasilar acantholysis that is histopathologically specific to PV was observed. Further, use of the fact that ETA produced by *Staphylococcus aureus* specifically digests Dsg1, a small amount of ETA that does not induce apparent blister formation in itself was simultaneously injected. AK19 (FIG. 2g) and AK23 (FIG. 2h) both formed a gross extensive blister, and suprabasilar acantholysis that is histopathologically specific to PV was observed. Immunohistologically, in all of the combinations in direct immunofluorescence, deposition of antibodies to the cell surface of epidermal keratinocytes just above the basal lamina was observed.

B-3 (Transplantation of Hybridomas to Immunodeficient Mice)

Figure 3:
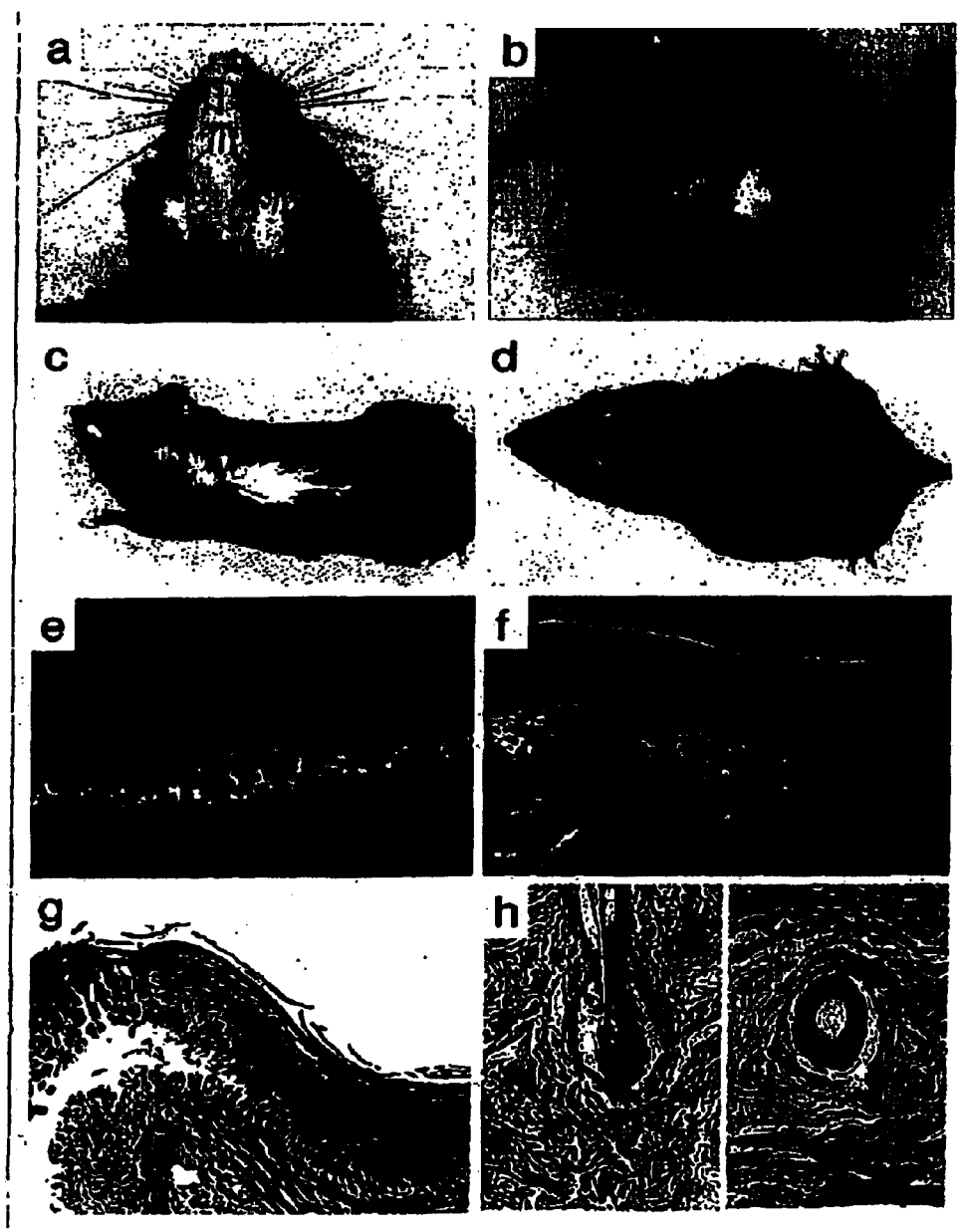
FIG. 3 is a photograph showing the results when the hybridoma producing the anti-Dsg3 monoclonal antibody AK23 of the present invention is inoculated into an immunodeficient mouse.

As mentioned above, in the experiment using neonatal mice skin, Dsg1 was coexpressed in mouse skin, and it was necessary to confirm the pathogenicity in order to specifically impair the adhesion function of that Dsg1 by simultaneously transferring PF patient sera or ETA. Therefore, in order to confirm the pathogenicity due to the use of monoclonal antibodies alone, 8 hybridoma clones were inoculated intraperitoneally into immunodeficient mice, respectively, made to be an ascite, and the change in the phenotypes was observed. It was considered that blister is formed at the oral mucosa if the antibody has a pathogenicity (FIG. 3). As a result, in Rag2$^{-/-}$ mice inoculated with AK23-producing hybridomas, hair loss was observed around the mouth (FIG. 3a), around the eyes (FIG. 3b) and at the back (FIG. 3c), and from day 7 to day 9, the mice died suddenly before the development of ascites formation. In Rag2$^{-/-}$ mice inoculated with AK19-producing hybridomas, although ascites formation (FIG. 3d) was observed, no phenotype such as hair loss was observed. In direct immunofluorescence, AK23 (FIG. 3e) and AK19 (FIG. 3f) both showed IgG deposition to the surface of the keratinocytes in the site that accord with the Dsg3 distribution of hard palate mucous membrane. However, histopathologically, disruption of cell-cell adhesion was observed only in Rag2$^{-/-}$ mice inoculated with AK23-producing hybridoma (FIG. 3g; hard palate, h; skin, telogen hair club). These gross, histopathologic changes were the same as those of Dsg3$^{-/-}$ mice. However, in mice wherein monoclonal antibody producing hybridomas that produce monoclonal antibodies aside from AK23, such as AK20 and AK19, were intraperitoneally inoculated, IgG deposition the same as in AK23 was observed immunohistologically in the plantar skin and hard palate mucosa. However, although sufficient ascites formation was observed, gross hair loss, weight loss was not observed, and immunohistologically, suprabasilar acantholysis was not observed (Table 5). Based on these results, it was confirmed that AK23 is an antibody having a pathological activity that can induce pemphigus lesions by itself.

TABLE 5

| | Immunohistological finding | Histopathological finding | Gross phenotype | |
|---|---|---|---|---|
| | Direct immunofluorescence | Suprabasilar acantholysis | Hair loss | Weight loss |
| AK23 | + | + | + | + |
| AK19 | + | − | − | − |
| AK20 | + | − | − | − |

The pathogenic activity of monoclonal antibodies such as AK23 (AK) was further examined also for adult mice 4-weeks old or older from the viewpoint of passive transfer and ascites formation. The results of analysis are shown in Table 6. Monoclonal antibody alone, a combination of monoclonal antibody and PF IgG (AK+PF IgG) or a combination of monoclonal antibody and ETA (AK+ETA) was injected into the adult mice, then observed whether gross blister and microscopic blister was formed 18 to 24 hours later, and as a result, typical histological PV finding was observed in adult mice found to have gross blisters. Further, hybridomas were inoculated intraperitoneally to Rag2$^{-/-}$ mice 4-weeks old or older, and gross hair loss and ascites formation was observed 7 to 10 days after inoculation in AK23-producing hybridoma inoculated groups. The antibody titers of mice with AK15, AK19 and AK20 were 4 times or more higher than that of mice with AK23, excluding the possibility that the low induction ability of blister formation was due to insufficient amount of the antibody production. These findings indicate that AK1, AK7, AK9, AK15, AK18, AK19 and AK20 do not have the ability to induce the loss of cell-cell adhesion of keratinocytes in adult mice. AK23 induced the blister formation with the typical PV phenotype in both passive transfer and ascites formation assays, while AK19 generated the PV blister formation only in passive transfer assay. The other monoclonal antibodies did not show pathogenicity in either assays.

TABLE 6

| | Passive Transfer | | | | | | | |
|---|---|---|---|---|---|---|---|---|
| | | AK alone | | | AK + PF IgG | | AK + ETA | |
| | | IgG | blister formation | | | gross | | gross |
| AK | n | deposition | microscopic | gross | n | blister | n | blister |
| 1 | 7 | + | 0 | 0 | 22 | 0 | | ND |
| 7 | 4 | + | 0 | 0 | 7 | 0 | | ND |
| 9 | 5 | + | 0 | 0 | 9 | 0 | | ND |
| 15 | 5 | + | 0 | 0 | 2 | 0 | | ND |
| 18 | 2 | + | 0 | 0 | 5 | 0 | | ND |
| 19 | 10 | + | 7 | 0 | 12 | 10 | 6 | 2 |
| 20 | 6 | + | 0 | 0 | 10 | 0 | | ND |
| 23 | 5 | + | 5 | 0 | 7 | 7 | 6 | 6 |

| | Ascites Formation | | | |
|---|---|---|---|---|
| AK | n | anti-Dsg3 IgG antibody titer | in vivo IgG deposition | PV phenotype |
| 1 | 10 | ND | + | 0 |
| 7 | 10 | ND | + | 0 |
| 9 | 10 | ND | + | 0 |
| 15 | 2 | 289.1 ± 3.2 | + | 0 |
| 18 | 5 | 21.1 ± 13.5 | + | 0 |
| 19 | 4 | 356.2 ± 10.4 | + | 0 |

TABLE 6-continued

| 20 | 5 | 388.8 ± 9.6 | + | 0 |
|----|---|-------------|---|---|
| 23 | 9 | 64.5 ± 13.2 | + | 9 |

B-4 (Examination of the Antigen Specificity of Monoclonal Antibodies by Immunoprecipitation)

In order to analyze the epitopes on Dsg3 recognized by the monoclonal antibodies, domain-swapped molecules and molecules including the full length of Dsg3 and Dsg1 extracellular domains (the amino acid residues 25-566, 65-566, 87-566, 1-88, 1-63, 1-34, 1-26, 1-10 of Dsg3 and the 8 types of domain-swapped molecules wherein their deleted region is substituted with Dsg1, that is, $Dsg1^{1-24}/Dsg3^{25-566}$, $Dsg1^{1-64}/Dsg3^{65-566}$, $Dsg1^{1-87}/Dsg3^{85-566}$, $Dsg3^{1-88}/Dsg1^{89-496}$, $Dsg3^{1-63}/Dsg1^{63-496}$, $Dsg3^{1-34}/Dsg1^{35-496}$, $Dsg3^{1-26}/Dsg1^{26-496}$, $Dsg3^{1-10}/Dsg1^{11-496}$) obtained from the baculovirus expression system, were constructed. Then, examination was conducted by immunoprecipitation. The results are shown in FIG. 4. FIG. 4 shows the schematic diagram of Dsg3-His and Dsg1-His having entire extracellular domain (EC1 to EC5) of Dsg3 and Dsg1, and the His-tag of C terminal was used for purification of proteins using Ni-NTA column.

As can be seen from FIG. 4, all of AK23, AK20 and AK19 showed reactivity to Dsg3-His having the entire extracellular domain of Dsg3, but not to Dsg1-His having the entire extracellular domain of Dsg1. The results confirmed that the monoclonal antibodies AK23, AK20 and AK19 mentioned above are antibodies that specifically recognize Dsg3. Further, it was confirmed that: AK23 has reactivity only to $Dsg3^{1-88}/Dsg1^{89-496}$ and $Dsg3^{1-63}/Dsg1^{63-496}$ molecules; the epitopes recognized by AK23 are present in the 1 to 63 amino acid residues of the N terminal Dsg3 extracellular domain; and the epitopes recognized by AK20 and AK19 are present in the 87 to 566 amino acid residues from the N terminal of the Dsg3 extracellular domain, that is, at the C terminal side from the Dsg3 amino acid residue 87.

Figure 6:
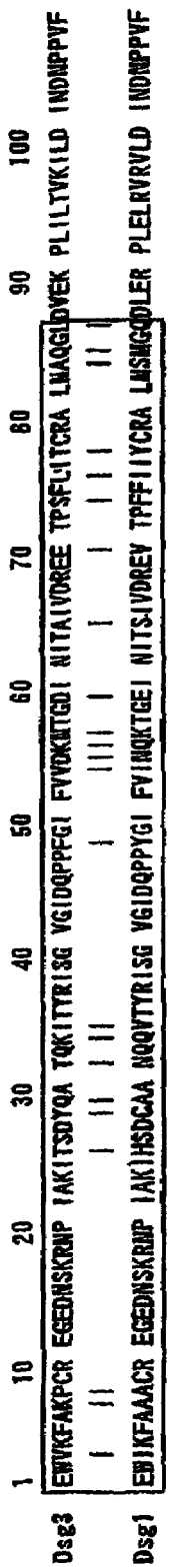
FIG. 6 is a view showing the comparison of the amino acid sequences in the EC1 region of Dsg3 (SEQ ID NO: 1) and Dsg1 (SEQ ID NO:2). The full amino acid sequences of the Dsg3 and Dsg1 regions shown in FIG. 6 corresponds to SEQ ID NO: 56 and 57 respectively.
Figure 7:
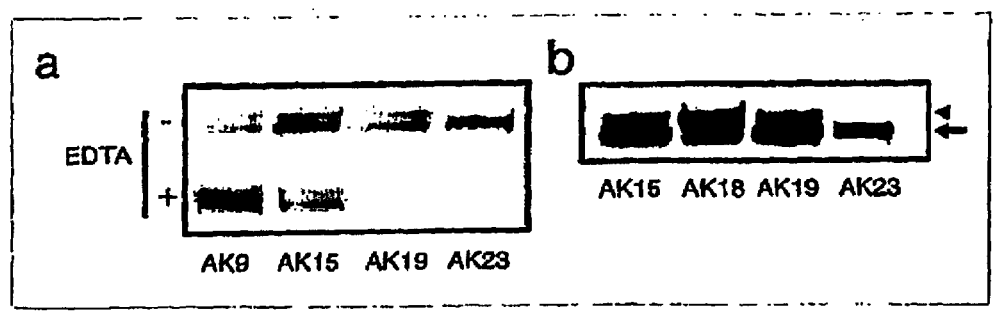
FIG. 7 is a photograph showing the results of reaction between the anti-Dsg3 monoclonal antibody of the present invention and antigen Dsg3 by immunoprecipitation.

Dsg3 and Dsg1, which are desmosomal cadherins, are known for the high homology of their amino acid sequences. FIG. 6 shows the amino acid sequence in the EC1 domain of Dsg3 and Dsg1, with the comparison of the left side as the N terminal and right side as the C terminal. In order to further examine the epitopes of AK23 mentioned above in more detail, point-mutated molecules wherein only the Dsg1- and Dsg3-specific amino acids in the amino acid 1-87 of the Dsg3 and Dsg1 extracellular domains are introduced by point-mutation, was used and immunoprecipitation was conducted. The results are shown in FIG. 5. As shown in FIG. 5, AK23 retained the reactivity with the point-mutated Dsg3 molecules (Dsg3-M1, M2, M3, M4, M5, M6, M1-2, M1-2-3) wherein the Dsg3-specific amino acid 25-56 domains and 70-84 domains are substituted with Dsg1-specific amino acids, and lost the reactivity with the point-mutated molecules (Dsg1-M1-2, M1-2-3) wherein the Dsg1-specific amino acid 25-56 domains are substituted with Dsg3-specific amino acids. It was considered from these results that the epitopes of AK23 are present in the Dsg3 amino acid 1-87 domains except 25-56 domains.

The present inventors focused on the domains of Dsg3 N terminal, and used the point-mutated molecule Dsg3-M7 wherein only the amino acids V3, K7 and P8 were substituted with Dsg1-specific amino acid, and its reactivity was lost. Further, in Dsg1-M7 wherein Dsg1-specific I3, A7 and A8 were substituted with Dsg3-specific amino acid sequence, AK23 did not acquire reactivity. It was considered from these results that the amino acids V3, K7 and P8 of Dsg3 are necessary to the AK23 epitopes, however, not sufficient enough. Further, the present inventors constructed Dsg1-M7-8 wherein Dsg1-M7 was added with Dsg3-specific amino acid D59, and AK23 acquired reactivity. It was considered from the results above that the main epitope of AK23 is composed of at least one of the amino acids V3, K7 and P8, and D59, on the Dsg3 molecules. Dsg3-M8, wherein the Dsg3-specific amino acid D59 was substituted with Dsg1-specific amino acid E59 was used, and it was found that its reactivity was retained. This suggests that the Dsg3-specific amino acid D59 loses reactivity, dependently to at least one of the amino acids V3, K7 and P8 on the Dsg3 molecules.

To characterize the epitopes of monoclonal antibodes such as AK23 and the like, it was first determined whether the binding to Dsg3 of the antibodies is calcium-dependent or not. Recombinant mouse Dsg3-His was treated with or without EDTA, and then subjected to immunoprecipitation with the AK antibodies. EDTA treatment abolished the reactivity of AK19 and AK23 antibodies, but not the reactivity of the other AK antibodies (Table 3, FIG. 7*a*). When ELISA plate coated with mouse Dsg was treated with EDTA, similarly AK19 and AK23 lost binding and the binding of the other AK antibodies was not significantly affected. Therefore, it can be said that AK19 and AK23 recognize calcium-dependent epitopes, while the other AK antibodies recognize calcium-independent epitopes. Next, the reactivity against Dsg3 of AK23, AK19 and the like mentioned above was examined by immunoblotting. As a result, AK19, for example, showed reactivity against 2 types of proteins with different molecular weight. On the other hand, in AK23, only one band similar to the protein with small molecular weight observed in AK19 and the like, was found (FIG. 7*b*). The recombinant Dsg3 protein obtained from the baculovirus expression type has, in its culture supernatant, an inactivated Dsg3 protein having a pro-sequence and an active Dsg3 protein wherein the pro-sequence is cleaved. The protein with large molecular weight recognized only by AK19 is considered to be an inactivated Dsg3 protein having a pro-sequence. In comparison, AK23recognized only the protein molecules with small molecular weight. These findings reveal that AK23 recognizes only the so called activated Dsg3 protein wherein the pro-sequence is eliminated. Considering that the pro-sequence exists to prevent the molecules from adhering and aggregating in the process of protein synthesis, it is thought that AK23 recognizes the important site in Dsg3 adhesion function, and this accords with the results of epitope mapping mentioned above.

Recently, the three dimensional structure of the entire extracellular domain of C-cadherin was revealed by crystal structure analysis (Science 296, 1308-1313, 2002). Cadherin molecules adhere to each other at the EC1 domain of N terminal, and the amino acid sequence that comprises the adhesion surface was revealed. In that report, it was confirmed that the adhesion surface of C-cadherin is composed of amino acids 1 to 8, 20, 23 to 27 and 59 of its N terminal domain. By putting together these information and the results of the AK23 epitopes this time, it was revealed that V3, K7, P8 and D59 consequently exist on amino acid 1-8, 59 (see the hatched box in FIG. 5) which comprise the adhesion surface of its C-cadherin. These support that AK23 binds to the cadherin adhesion surface that is most important in the Dsg3 molecule function, and that blister is formed by directly impairing that cell-cell adhesive function.

The base sequence of the variable region (heavy chain, light chain) of the monoclonal antibody AK23 having said strong pathogenicity was determined by conventional methods. The base sequence and the amino acid sequence in the variable region (heavy chain, light chain) of AK23 are shown in FIG. 8.

INDUSTRIAL APPLICABILITY

According to the present invention, the elucidation of the onset mechanism of pemphigus vulgaris at the molecular level, a monoclonal antibody having a pathological activity that can induce pemphigus lesion, which is considered to be useful for the development of antigen-specific antibody elimination therapy, a peptide specifically recognized by the monoclonal antibody and considered to be useful as a therapeutic drug for pemphigus autoimmune disease, etc. are provided.

The invention claimed is:

1. A peptide containing an epitope specifically recognized by a monoclonal antibody comprising an H chain which has the amino acid sequence shown in SEQ ID NO: 4 and functions as an H chain of an anti-human Dsg3 monoclonal Fab antibody and an L chain which has the amino acid sequence shown in SEQ ID NO: 6 and functions as an L chain of an anti-human Dsg3 monoclonal Fab antibody, wherein the peptide is a) a point-mutated human Dsg3 molecule comprising T25H, Y28C and Q29A mutations and no other mutations in SEQ ID NO: 56, b) a point-mutated human Dsg3 molecule comprising T31N, K33Q and I34V mutations and no other mutations in SEQ ID NO: 56, c) a point-mutated human Dsg3 molecule comprising V53I, D54N, K55Q and N56K mutations and no other mutations in SEQ ID NO: 56, d) a point-mutated human Dsg3 molecule comprising E70V and S73F mutations and no other mutations in SEQ ID NO: 56, e) a point-mutated human Dsg3 molecule comprising L75I and T77Y mutations and no other mutations in SEQ ID NO: 56, f) a point-mutated human Dsg3 molecule comprising A83S and Q84M mutations and no other mutations in SEQ ID NO: 56, g) a point-mutated human Dsg3 molecule comprising T25H, Y28C, Q29A, T31N, K33Q and I34V mutations and no other mutations in SEQ ID NO: 56, h) a point-mutated human Dsg3 molecule comprising T25H, Y28C, Q29A, T31N, K33Q, I34V, F48Y, V53I, D54N, K55Q and N56K mutations and no other mutations in SEQ ID NO: 56, i) a point-mutated human Dsg3 molecule comprising a D59E mutation and no other mutations in SEQ ID NO: 56, or j) a point-mutated human Dsg1 molecule comprising I3V, A7K, A8P and E59D mutations and no other mutations in SEQ ID NO: 57.

* * * * *

SEQUENCE LISTING

```
<160> NUMBER OF SEQ ID NOS: 55

<210> SEQ ID NO 1
<211> LENGTH: 63
<212> TYPE: PRT
<213> ORGANISM: Homo sapiens

<400> SEQUENCE: 1

Glu Trp Val Lys Phe Ala Lys Pro Cys Arg Glu Gly Glu Asp Asn Ser
 1               5                  10                  15

Lys Arg Asn Pro Ile Ala Lys Ile Thr Ser Asp Tyr Gln Ala Thr Gln
            20                  25                  30

Lys Ile Thr Tyr Arg Ile Ser Gly Val Gly Ile Asp Gln Pro Pro Phe
        35                  40                  45

Gly Ile Phe Val Val Asp Lys Asn Thr Gly Asp Ile Asn Ile Thr
    50                  55                  60

<210> SEQ ID NO 2
<211> LENGTH: 63
<212> TYPE: PRT
<213> ORGANISM: Homo sapiens

<400> SEQUENCE: 2

Glu Trp Val Lys Phe Ala Lys Pro Cys Arg Glu Arg Glu Asp Asn Ser
 1               5                  10                  15

Arg Arg Asn Pro Ile Ala Lys Ile Thr Ser Asp Phe Gln Lys Asn Gln
            20                  25                  30

Lys Ile Thr Tyr Arg Ile Ser Gly Val Gly Ile Asp Gln Pro Pro Phe
        35                  40                  45

Gly Ile Phe Val Val Asp Pro Asn Asn Gly Asp Ile Asn Ile Thr
    50                  55                  60

<210> SEQ ID NO 3
<211> LENGTH: 347
<212> TYPE: DNA
<213> ORGANISM: Homo sapiens
<220> FEATURE:
<221> NAME/KEY: CDS
<222> LOCATION: (1)..(345)

<400> SEQUENCE: 3 cag gtc caa ctg cag cag tct ggg act gaa ctg gtg aag cct ggg gct    48
Gln Val Gln Leu Gln Gln Ser Gly Thr Glu Leu Val Lys Pro Gly Ala
 1               5                  10                  15 tca gtg aag ctg tcc tgc aag tct tct ggc tac acc ttc acc agc tac    96
Ser Val Lys Leu Ser Cys Lys Ser Ser Gly Tyr Thr Phe Thr Ser Tyr
            20                  25                  30 tgg ata aac tgg gtg aag cag agg cct gga cag ggc ctt gag tgg att   144
Trp Ile Asn Trp Val Lys Gln Arg Pro Gly Gln Gly Leu Glu Trp Ile
        35                  40                  45 gga aat att aat cct agc aat ggt ggt att aac tat aat gag aag ttc   192
```

```
Gly Asn Ile Asn Pro Ser Asn Gly Gly Ile Asn Tyr Asn Glu Lys Phe
        50                  55                  60 aag agt aag gcc aca ctg act gta gac aaa tcc tcc agc aca gcc tac    240
Lys Ser Lys Ala Thr Leu Thr Val Asp Lys Ser Ser Ser Thr Ala Tyr
 65                  70                  75                  80 atg caa ctc aag agc ctg aca tct gag gac tct gcg gtc tat tat tgt    288
Met Gln Leu Lys Ser Leu Thr Ser Glu Asp Ser Ala Val Tyr Tyr Cys
                 85                  90                  95 gca agg ggc ggc tat gat ggt tac ccc tgg ggc caa ggc acc acg gtc    336
Ala Arg Gly Gly Tyr Asp Gly Tyr Pro Trp Gly Gln Gly Thr Thr Val
            100                 105                 110 acc gtt tcc tc                                                     347
Thr Val Ser
        115

<210> SEQ ID NO 4
<211> LENGTH: 115
<212> TYPE: PRT
<213> ORGANISM: Homo sapiens

<400> SEQUENCE: 4

Gln Val Gln Leu Gln Gln Ser Gly Thr Glu Leu Val Lys Pro Gly Ala
 1               5                  10                  15

Ser Val Lys Leu Ser Cys Lys Ser Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Asn Pro Ser Asn Gly Gly Ile Asn Tyr Asn Glu Lys Phe
    50                  55                  60

Lys Ser Lys Ala Thr Leu Thr Val Asp Lys Ser Ser Ser Thr Ala Tyr
 65                  70                  75                  80

Met Gln Leu Lys Ser Leu Thr Ser Glu Asp Ser Ala Val Tyr Tyr Cys
                 85                  90                  95

Ala Arg Gly Gly Tyr Asp Gly Tyr Pro Trp Gly Gln Gly Thr Thr Val
            100                 105                 110

Thr Val Ser
        115

<210> SEQ ID NO 5
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 5 gac att cag atg aca cag tct ccc aaa ttc ctg ctt gta tca gca gga     48
Asp Ile Gln Met Thr Gln Ser Pro Lys Phe Leu Leu Val Ser Ala Gly
 1               5                  10                  15 gac agg gtt acc ata acc tgc aag gcc agt cag agt gtg agt tat gat     96
Asp Arg Val Thr Ile Thr Cys Lys Ala Ser Gln Ser Val Ser Tyr Asp
            20                  25                  30 gta gct tgg tat caa cag aag cca ggg cag tct ccg aaa ttg ctg ata    144
Val Ala Trp Tyr Gln Gln Lys Pro Gly Gln Ser Pro Lys Leu Leu Ile
        35                  40                  45 tcc tat gca tcc aat cgc tac act gga gtc cct gat cgc ttc act ggc    192
Ser Tyr Ala Ser Asn Arg Tyr Thr Gly Val Pro Asp Arg Phe Thr Gly
    50                  55                  60 agt gga tat ggg tcg gat ttc act ttc acc atc agc act gtg cag act    240
```

```
Ser Gly Tyr Gly Ser Asp Phe Thr Phe Thr Ile Ser Thr Val Gln Thr
 65                  70                  75                  80 gaa gac ctg gca gtt tat ttc tgt cag cag gat tat agc tct ccg tgg       288
Glu Asp Leu Ala Val Tyr Phe Cys Gln Gln Asp Tyr Ser Ser Pro Trp
                 85                  90                  95 acg ttc ggt gga ggc acc aag ctg gag ctg aaa cgt                       324
Thr Phe Gly Gly Gly Thr Lys Leu Glu Leu Lys Arg
            100                 105

<210> SEQ ID NO 6
<211> LENGTH: 108
<212> TYPE: PRT
<213> ORGANISM: Homo sapiens

<400> SEQUENCE: 6

Asp Ile Gln Met Thr Gln Ser Pro Lys Phe Leu Leu Val Ser Ala Gly
 1               5                  10                  15

Asp Arg Val Thr Ile Thr Cys Lys Ala Ser Gln Ser Val Ser Tyr Asp
                20                  25                  30

Val Ala Trp Tyr Gln Gln Lys Pro Gly Gln Ser Pro Lys Leu Leu Ile
            35                  40                  45

Ser Tyr Ala Ser Asn Arg Tyr Thr Gly Val Pro Asp Arg Phe Thr Gly
     50                  55                  60

Ser Gly Tyr Gly Ser Asp Phe Thr Phe Thr Ile Ser Thr Val Gln Thr
 65                  70                  75                  80

Glu Asp Leu Ala Val Tyr Phe Cys Gln Gln Asp Tyr Ser Ser Pro Trp
                 85                  90                  95

Thr Phe Gly Gly Gly Thr Lys Leu Glu Leu Lys Arg
            100                 105

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence:Primer 1

<400> SEQUENCE: 7
gaagatctcc tataaatatg gactggagtt tcttcagag                             39

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:Primer 2

<400> SEQUENCE: 8
cggactagta attttggcga ttgggtt                                          27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:Primer 3

<400> SEQUENCE: 9
gccactagtg attaccaagc aacccag                                          27

<210> SEQ ID NO 10
<211> LENGTH: 28
```

-continued

```
<212> TYPE: DNA
<213> ORGANISM: Artificial Sequence
<220> FEATURE:
<223> OTHER INFORMATION: Description of Artificial Sequence:Primer 4

<400> SEQUENCE: 10
cctgctcgag cctccctgag tgcggcct                                              28

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:Primer 5

<400> SEQUENCE: 11
cggactagtt atattaattt caccagt                                               27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:Primer 6

<400> SEQUENCE: 12
gccactagta tagtcgaccg ggaggaa                                               27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:Primer 7

<400> SEQUENCE: 13
cgggacgtct tggcccattg agttcag                                               27

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:Primer 8

<400> SEQUENCE: 14
gccgacgtcg agaaaccact tatacta                                               27

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence:Primer 9

<400> SEQUENCE: 15
ctggtttgca gcacaatctg agtgaatctt ggcaattggg tttcttttt                       48

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:Primer 10

<400> SEQUENCE: 16
```
ttactgccat ccagttagct gaga                                      24

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:Primer 11

<400> SEQUENCE: 17
gacaaccatg gggctcttcc ccagaactac                                30

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence:Primer 12

<400> SEQUENCE: 18
ttgccaaacc ctgcagaatc aagttcgcag cagcctgtcg t                   41

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:Primer 13

<400> SEQUENCE: 19
gccactagtg attgtgctgc aaaccag                                   27

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence:Primer 14

<400> SEQUENCE: 20
cttgtcgaca tgtacattgt ctgataacaa atc                            33

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence:Primer 15

<400> SEQUENCE: 21
gaagatctcc tataaatatg gggctcttcc ccag                           34

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:Primer 16

<400> SEQUENCE: 22
cggactagta atcttggcaa ttgggtt                                   27

<210> SEQ ID NO 23
<211> LENGTH: 40
<212> TYPE: DNA
<213> ORGANISM: Artificial Sequence

```
<220> FEATURE:
<223> OTHER INFORMATION: Description of Artificial Sequence:Primer 17

<400> SEQUENCE: 23
ccaagcaacc cagaaaatca cataccgcat ctctggagta                              40

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence:Primer 18

<400> SEQUENCE: 24
tgctgcgaac ttgattctgc agggtttggc aaatttcacc ca                          42

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:Primer 19

<400> SEQUENCE: 25
gccactagta tagttgatcg agaggtc                                            27

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence:Primer 20

<400> SEQUENCE: 26
cggactagtt atgttaatat ctccagt                                            27

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence:Primer 21

<400> SEQUENCE: 27
gccgacgtcg agaggcctct agagctc                                            27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence:Primer 22

<400> SEQUENCE: 28
cgggacgtct agtccttggg catttag                                            27

<210> SEQ ID NO 29
<211> LENGTH: 56
<212> TYPE: DNA
<213> ORGANISM: Artificial Sequence
<220> FEATURE:
<223> OTHER INFORMATION: Description of Artificial Sequence:Primer 23

<400> SEQUENCE: 29
gaaacccaat tgccaagatt cattcagatt gcgcagcaac ccagaaaatc acctac           56
```

<210> SEQ ID NO 30
<211> LENGTH: 49
<212> TYPE: DNA
<213> ORGANISM: Artificial Sequence
<220> FEATURE:
<223> OTHER INFORMATION: Description of Artificial Sequence:Primer 24

<400> SEQUENCE: 30
acttcagatt accaagcaaa ccagcaagtc acctaccgaa tctctggag            49

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence:Primer 25

<400> SEQUENCE: 31
ggccgccttt tggaatcttt gttattaacc aaaaaactgg agatattaac ataacag    57

<210> SEQ ID NO 32
<211> LENGTH: 48
<212> TYPE: DNA
<213> ORGANISM: Artificial Sequence
<220> FEATURE:
<223> OTHER INFORMATION: Description of Artificial Sequence:Primer 26

<400> SEQUENCE: 32
gctatagtcg accgggaggt aactccattc ttcctgatca catgtcgg             48

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence:Primer 27

<400> SEQUENCE: 33
gaggaaactc caagcttcat catctattgt cgggctctaa atgcc                45

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence:Primer 28

<400> SEQUENCE: 34
catgtcgggc tctaaatagc atgggactag atgtagag                        38

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence:Primer 29

<400> SEQUENCE: 35
gacaaccatg gggctcttcc ccagaactac                                 30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:Primer 30

-continued

<400> SEQUENCE: 36
gcagccatgg actggagttt cttcagagta                                    30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence:Primer 31

<400> SEQUENCE: 37
cggactagtg aggaacatgg gtgtgccagc                                    30

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence:Primer 32

<400> SEQUENCE: 38
ttactgccat ccagttagct gaga                                          24

<210> SEQ ID NO 39
<211> LENGTH: 48
<212> TYPE: DNA
<213> ORGANISM: Artificial Sequence
<220> FEATURE:
<223> OTHER INFORMATION: Description of Artificial Sequence:Primer 33

<400> SEQUENCE: 39
ctggtttgca gcacaatctg agtgaatctt ggcaattggg tttctttt                48

<210> SEQ ID NO 40
<211> LENGTH: 48
<212> TYPE: DNA
<213> ORGANISM: Artificial Sequence
<220> FEATURE:
<223> OTHER INFORMATION: Description of Artificial Sequence:Primer 34

<400> SEQUENCE: 40
gattgtgctg caaaccagca agttacctac cgaatctctg gagtggga                48

<210> SEQ ID NO 41
<211> LENGTH: 88
<212> TYPE: DNA
<213> ORGANISM: Artificial Sequence
<220> FEATURE:
<223> OTHER INFORMATION: Description of Artificial Sequence:Primer 35

<400> SEQUENCE: 41
atcaattcct actccagaga tgcggtatgt aacttgctgg tttgcagcac aatctgagtg   60
aatcttggca attgggtttc tttttgag                                      88

<210> SEQ ID NO 42
<211> LENGTH: 85
<212> TYPE: DNA
<213> ORGANISM: Artificial Sequence
<220> FEATURE:
<223> OTHER INFORMATION: Description of Artificial Sequence:Primer 36

<400> SEQUENCE: 42
cgcatctctg gagtaggaat tgatcagcca ccatatggga tctttgtcat taatcagaaa   60

-continued

<210> SEQ ID NO 43
<211> LENGTH: 48
<212> TYPE: DNA
<213> ORGANISM: Artificial Sequence
<220> FEATURE:
<223> OTHER INFORMATION: Description of Artificial Sequence:Primer 37

<400> SEQUENCE: 43
ctgggttgct tggtaatctg aagtaatttt ggcgattggg ttcctctt       48

<210> SEQ ID NO 44
<211> LENGTH: 49
<212> TYPE: DNA
<213> ORGANISM: Artificial Sequence
<220> FEATURE:
<223> OTHER INFORMATION: Description of Artificial Sequence:Primer 38

<400> SEQUENCE: 44
gattaccaag caacccagaa aatctaccgc atctctggag taggaattg      49

<210> SEQ ID NO 45
<211> LENGTH: 87
<212> TYPE: DNA
<213> ORGANISM: Artificial Sequence
<220> FEATURE:
<223> OTHER INFORMATION: Description of Artificial Sequence:Primer 39

<400> SEQUENCE: 45
atcgattccc actccagaga ttcggtaggt gattttctgg gttgcttggt aatctgaagt   60
aattttggcg attgggttcc tctttga                              87

<210> SEQ ID NO 46
<211> LENGTH: 88
<212> TYPE: DNA
<213> ORGANISM: Artificial Sequence
<220> FEATURE:
<223> OTHER INFORMATION: Description of Artificial Sequence:Primer 40

<400> SEQUENCE: 46
cgaatctctg gagtgggaat cgatcagccg cctttttggaa tctttgttgt tgacaaaaac   60
actggtgaaa ttaatataac atccatag                             88

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence:Primer 41

<400> SEQUENCE: 47
cttctctgca ggcagcggca aatttgatcc attcacgttt                40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence:Primer 42

<400> SEQUENCE: 48
tgaatggatc aaatttgccg ctgcctgcag agaaggagaa                40

```
<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence:Primer 43

<400> SEQUENCE: 49
aaaaacactg gagaaattaa cataacagc                                    29

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence:Primer 44

<400> SEQUENCE: 50
tgttatgtta atttctccag tgtttttgtc                                   30

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence:Primer 45

<400> SEQUENCE: 51
tgaatgggtg aagttcgcaa aaccctgtcg tgaaggtgaa                        40

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence:Primer 46

<400> SEQUENCE: 52
cttcacgaca gggttttgcg aacttcaccc attcacgttt                        40

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence:Primer 47

<400> SEQUENCE: 53
aaactggtga tattaatata acatcc                                       26

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence:Primer 48

<400> SEQUENCE: 54
atattaatat caccagtttt ctgatt                                       26

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence:Mutagenic
      primer
```

-continued

<400> SEQUENCE: 55

```
gacttggttg aatactcacc ag                                            22
```